(12) United States Patent
Gilbert et al.

(10) Patent No.: US 7,572,903 B1
(45) Date of Patent: Aug. 11, 2009

(54) METHOD OF REGULATION OF BACTERIAL PERSISTER STATUS

(75) Inventors: Peter Gilbert, Cheshire (GB); Alexander H. Rickard, Binghamton, NY (US); Michael Kertesz, Sale (GB); Sharon Lindsay, Liverpool (GB)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 11/505,644

(22) Filed: Aug. 17, 2006

Related U.S. Application Data

(60) Provisional application No. 60/709,224, filed on Aug. 18, 2005.

(51) Int. Cl.
*C07H 21/04* (2006.01)
*C07H 21/02* (2006.01)
*C12N 9/00* (2006.01)
*C12N 15/01* (2006.01)

(52) U.S. Cl. .......... 536/23.7; 424/9.1; 424/9.2; 435/183; 435/440; 435/441; 435/446; 435/471; 536/23.1

(58) Field of Classification Search .......... 424/9.1, 424/9.2; 435/440, 441, 446, 471, 183; 536/23.1, 536/23.7
See application file for complete search history.

(56) References Cited

OTHER PUBLICATIONS

Gilbert P, et al., "The physiology and collective recalcitrance of microbial biofilm communities," Adv. Microb. Physiol. 46:202-256 (2002).
Keren I, et al., "Persister cells and tolerance to antimicrobials," FEMS Microbiol. Lett. 230:13-18 (2004).

*Primary Examiner*—Rodney P. Swartz

(57) ABSTRACT

In one embodiment, the present invention is a method of controlling persister status in a bacterial cell population comprising the step of modulating the expression of native chromosomal sequences disclosed in Table 8.

8 Claims, 5 Drawing Sheets

US 7,572,903 B1

METHOD OF REGULATION OF BACTERIAL PERSISTER STATUS

CROSS-REFERENCE TO RELATED APPLICATION

This application claims the benefit of U.S. provisional application 60/709,224, filed Aug. 18, 2005 and incorporated by reference herein.

STATEMENT REGARDING FEDERALLY SPONSORED RESEARCH OR DEVELOPMENT

--

BACKGROUND OF THE INVENTION

The recalcitrance of biofilm communities to a wide range of antimicrobial treatments, including those involving antiseptics, disinfectants and antibiotics, has been pivotal towards the funding and study of biofilm physiology (Gilbert, et al., *Adv. Microb. Physiol.* 46:203-256, 2002). Intuitive explanations of recalcitrance, such as reaction diffusion, limitation of access, and phenotypic heterogeneity, fail to fully explain the phenomenon (Gilbert, et al., supra, 2002). Since the introduction of antibiotics in the 1940's microbiologists have observed that antimicrobial treatments often fail to completely eradicate the target microbial population (Bigger, *The Lancet* ii:497-499, 1994; Lewis, *Antimicro. Agents Chemo.* 45:999-1007,2001, Spoering, et al., *J. Bacterial.* 183:6746-6751, 2001; Suyfa, et al., *Science* 2003; Babalan, et al., *Science* 305:1622-1625, 2004; Levin, *Science* 305:1678-1679, 2004). The survivors, termed 'persisters' appear to be equally sensitive to treatments, when isolated and re-grown, as were the original progenitor population. This argues against chance mutations affecting susceptibility, and indicates a definite role for phenotypic heterogeneity within bacterial cultures and the temporary expression of a resistant phenotype by a small sub-set of cells.

For many bacterial infections, the presence of persisters does not affect the outcome of treatments (Lewis, supra, 2001). This is because the immune system is able to successfully combat such small numbers of surviving cells (Lewis, supra, 2001). In chronic, deep-seated infections, however, and in those associated with growth of the bacteria as biofilms, the persisters are retained within the residual biofilm matrix and physically protected from phagocytosis (Lewis, supra, 2001). Additionally such cells are nurtured by the concentration of nutrients released from a lysing susceptible population and are able to rapidly re-establish themselves post-treatment (Lewis, supra, 2001; Gilbert, et al., supra, 2002).

An intriguing hypothesis, recently proposed by the group of Kim Lewis (Northeastern University, Boston, USA), suggests that death from antimicrobial treatment relates to an induced autolysis of sub-lethally damaged organisms (apoptosis) (Lewis, *Microbiol. Mole. Biol. Rev.* 64:503-514, 2000). Thus, regardless of the mechanisms of action of the treatment agent, bacterial death could be related to a singular response by the cells. Invocation of a singular mechanism of cell death enabled singular mechanisms of resistance to be postulated. Previous work had suggested that mutant cell lines defective in hipBA operon, and relE were substantially altered in their expression of the persistence phenomenon (Keren, et al., *FEMS Microbiol. Let.* 230:13-18, 2004).

relE is a general inhibitor of translation and is associated with slow growing or non-growing cells and over-expression causes a dramatic increase in the incidence of persistence. hipB is a transcriptional regulator and suppresses hipA (Black, et al., *J. Bacteriol.* 176:4081-4091, 1994). HipA does not show homology to any protein of known function but is postulated to encode a toxin-antitoxin module (Black, et al., *J. Bacteriol.* 173:5732-5739, 1991). The toxin component is relatively stable whilst the anti-toxin component is labile (Moyed, et al., *J. Bacteriol.* 166:399-403, 1986; Black, et al., supra, 1994; Falla, et al., *Antimicrob. Agents Chemo.* 42:3282-3284, 1998). Imbalance of the pair is thought to lead to cell death and subsequent cellular lysis. Thus, Lewis proposed that persistence related to loss, or suppression, of this hypothetical apoptotic mechanism.

Lewis (Keren, et al., supra, 2004) went on to examine the pattern of gene expression in isolated persister cells using DNA expression arrays. Persisters were obtained by treating an exponentially growing culture with a β-lactam antibiotic. Actively growing cells lysed as a result of defects in cell wall synthesis whilst the persisters, reputedly slow growing or quiescent (Sufya, et al., *J. App. Microbiol.* 95:1261-1267, 2003), did not succumb. Prolonged (180 min) incubation of the culture led to denaturation of that mRNA released from the lysed cells and enabled the persisters to be collected and their RNA to be extracted. Whilst the recovered persisters had undoubtedly tolerated the insult of antibiotic exposure they had also been exposed to ampicillin for a prolonged period and might have exhibited changes related to non-lethal actions of the agent. DNA expression arrays developed with the extracted RNA showed a number of genes and gene products to be up regulated. Several functional groups of genes were evident within the most upregulated 300 genes. These were found to represent the SOS response genes, recA, sulA and uvrBA together with umuDC; the phage shock (psp) operon genes, and several heat and cold shock genes. All of these patterns of gene expression were consistent with the persisters being slow growing or dormant but could not explain the phenomenon of persistence. Other genes were upregulated and represented toxin-antitoxin modules, including dinJlyafQ, yefM, relBE and mazEF, adding support to his proposed mechanisms of persistence (Lewis, supra, 2000; Kaldalu, et al., *Antimicrob. Agents Chemo.* 48:890-896, 2004; Keren, et al., supra, 2004).

BRIEF SUMMARY OF THE INVENTION

In one embodiment, the present invention is a method of altering bacterial persister status, comprising the steps of (a) identifying a bacterial population and (b) modulating the expression of a bacterial gene or gene product within the population wherein the gene is selected from the group described in Table 8, preferably the group consists of *E. coli* genes mcrA, lit, pin, ykgM and ykgK and bacterial genes corresponding to the *E. coli* genes mcrA, lit, pin, ykgM and ykgK. In one embodiment, the modulation is via antisense RNA, or through application of inhibitors or enhancers of mcrA, lit, pin, ykgM or ykgK gene expression products.

Preferably, the method suppresses ykgk gene expression or gene expression product or a gene or gene expression product of a bacterial gene corresponding to ykgk and the modulation decreases the level of persister cells.

Preferably, the modulation enhances ykgK gene expression or gene expression product or a gene or gene expression product of bacterial gene corresponding to ykgK and the modulation increases the level of persister cells.

Preferably, the modulation suppresses or enhances the ykgM gene or gene expression product or a gene or gene expression product of a bacterial gene corresponding to ykgM and wherein the modulation decreases the level of persister cells.

Preferably, the modulation increases the level of persister cells and enhances mcrA gene expression or gene expression product or a gene or gene expression product of a bacterial gene corresponding to mcrA.

Preferably, the modulation enhances or suppresses lit gene or gene expression product or a gene or gene expression product of a bacterial gene corresponding to lit and the modulation increases persister levels.

Preferably, the modulation enhances or suppresses the pin gene or gene expression product or a gene or gene expression product of a bacterial gene corresponding to pin and the modulation increases persister levels.

In another embodiment, the invention is a method of identifying compounds that alter bacterial persister status, comprising the step of identifying compounds that modulate the expression of a gene disclosed in Table 8, preferably selected from the group of E. coli genes mcrA, lit, pin, ykgM and ykgk and bacterial genes corresponding to mcrA, lit, pin, ykgM and ykgK or inhibit or enhance the protein products of these genes.

Other embodiments, features and advantages of the present invention would be apparent to one of skill in the art.

DETAILED DESCRIPTION OF THE INVENTION

Brief Background

Figure 1:
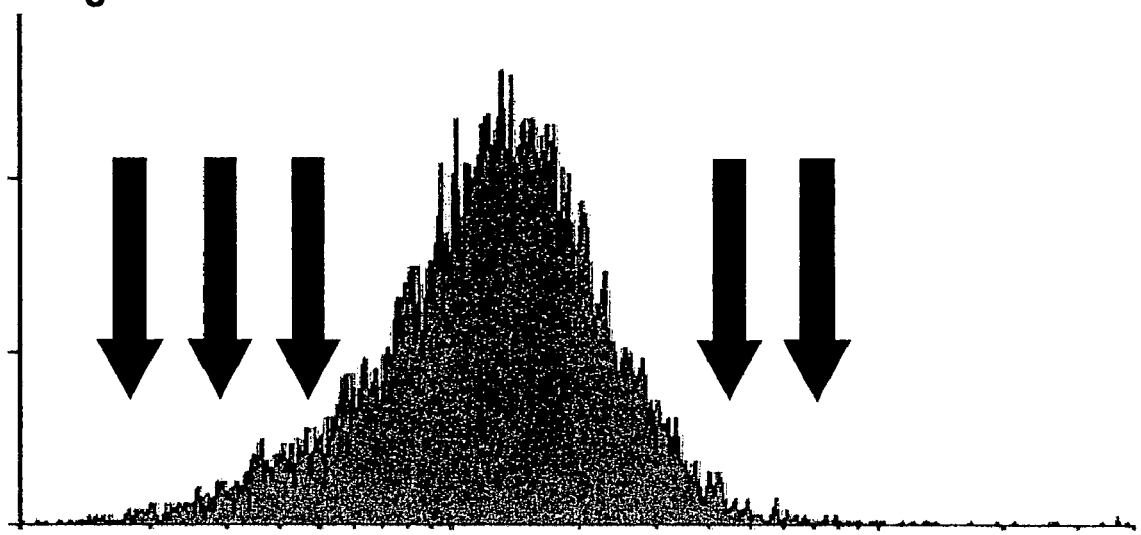
FIG. 1. Distributions of fluorescence intensity distribution in stationary phase cultures of E. coli K-12 C600::mTn5gusA-pgfp21 cultured for 16 hours in nutrient broth at 37° C.

As disclosed above, the persister state has been defined as a phenotype, present at low frequency within all bacterial populations, that is especially tolerant towards treatment with a diverse range of antimicrobial drugs. In biofilms, persisters contribute towards the chronicity and long-term survival of the community in the face of aggressive chemotherapy. Persister status has been suggested to relate to overexpression of the RelE toxin and HipA in a hypothesis relating cell death by antimicrobial treatments to apoptosis, and persistence to the adoption of an apoptosis-deficient phenotype. Such hypotheses stem from studies of HipA mutants and DNA expression arrays of the survivors of antimicrobials treatments (Keren, et al., *FEMS Microbiol. Let.* 230:13-18, 2004). Such studies depend upon the recovery of persisters following antibiotic treatment and arguably might reflect post-antibiotic effects rather than the causality of persistence.

In General

We have identified routes to the manifestation of persistence in microbial communities (biofilms):

(i) These routes embody two sets of prophage genes (Cp4-6 and e14) that encode toxin:antitoxin pairs of proteins. We hypothesize that differential expression of these pairs lead to an excess of the toxin (usually a transcriptional inhibitor) that will halt growth and thereby induce a tolerance to many antibiotics/biocides that act through corruption of the products of biosynthesis. (The CP4-6 toxin is encoded by ykfI; the antitoxin is encoded by yaFW; E14 toxin contains a gene (lit).) The e14 prophase, based on the T4 bacteriophage, contains a gene (lit) that encodes a translational inhibitor. In the wild-type phage; this ensures that bacterial protein synthesis ceases in favor of viral. In the prophage form the lit gene product might ensure a rapid transition to a persister phenotype, particularly in conjunction with a transcriptional inhibitor such as YafW. Blocking the expression of lit and/or yafW will alleviate persister status. Equally, over-expression will induce it.

(ii) While the levels of expression (measured by mRNA levels) are 1% in persisters relative to normal phenotypes, genes in positions 287628-365529 and in positions 1196090-1211226 were heavily upregulated and contained a number of the most highly expressed genes determined by microarray (i.e. mcrA). The first region contains at least three different classes of transcriptional regulators including IclR, (yagI), LysR (yahB), ARAC (ykgA, ykgD) and other unknown putative regulators: yapp, putative periplasmic regulator, betI, a bet gene repressor and prpR, a regulator of the prp system. The second gene region contains both positive and negative regulators of e14 prophage (b1146 and ymfL) and an MerR family regulator that activates sub-optimal sigma (70)-dependent promoters. This embodiment refers to regulators that are upregulated in the persister phenotype. For those target genes that encode translatable RNA, and thereby protein, the protein product becomes a valid target amenable to conventional approaches of rational drug design through (i) overproduction of the protein, (ii) determination of crystal structure through X-Ray crystallography and (iii) de-novo design of small chemical inhibitors. If one could block either their upregulation at a transcriptional level or sterically hinder their binding to DNA through use of specific blockers, then one would anticipate a loss of persister status.

(iii) A novel cascade of regulator control was also noted. The majority of the up-regulated genes/regions detected in the array experiments corresponded to small, classical intergenic regions (<300 nucleotides, lacking obvious promoters/start and stop codons). These corresponded to eleven of the top 22 gene products. Six other intergenic (IG) regions were up-regulated but these were large segments of the DNA and corresponded to identified genes on the antisense strands of which most appeared in the two upregulated hotspots (above). Of the classical IG's all possessed YUNR motifs (necessary for DNA and RNA binding) suggesting some regulatory function for a non-coding RNA. Significant sequence homologies were detected between these IG's and the remainder of the chromosome, particularly for other (secondary) IG's. In turn, the secondary IG showed high levels of homology with a third tier of intergenic regions many of which showed cross-homology back to the upregulated regions of the chromosome and to other primary and secondary IG regions. The numbers of IG's orf's connected in this way were; primary, six; secondary, 28; tertiary, 72. UP and downstream genes of the tertiary regions were slightly upregulated (p→85%). Knockouts of these classical, primary IG's are profoundly affected in terms of susceptibility towards biocides.

(iv) A list of candidate genes (Table 9, less the IG's) with open reading frames, and therefore associated with translation to protein, was constructed. A panel of isogenic mutant lines of *E. coli* were engineered that conditionally overexpressed these genes (lit, mcrA, pin, yagL, ykgK and ykgM). Other strains were developed where antisense RNA to the candidate genes could be conditionally expressed. Overexpression of antisense RNA will suppress the candidate RNA sequence. The conditional antisense knockout strains were constructed for lit, pin, ykgK and ykgM. Phenotypes for these genetically modified strains are given in Table 15 and 16. In summary, lit, pin, ykgK, ykgM and mcrA were profoundly affected in their expression of the persister phenotype. Notably, persisters could not be detected in antisense knockout strains grown to stationary phase and induced for the overexpression of antisense RNA towards pin, ykgK and ykgM, and were reduced 4-fold for antisense to mcrA. Bioinformatic searches with respect to these RNA sequences identified many homologous sequences in related and unrelated genera. These data validate the proposed genes as targets directed against the persister phenotype against a broad spectrum of bacterial types.

Identification of these targets offers a number of ways to control persister status. Therefore, the methods of the present invention include:

(i) Control of persister status by use of inhibitors of positive and negative regulators of the two hot-spot regions of the chromosome.

(ii) Control of persister status by use of inhibitors of the toxin: antitoxin protein pairs associated with prophage CP4-6 and e14 and of antitoxin analogues.

(iii) Control of persister status by use of inhibitors of primary IG's identified in the array through knowledge of secondary structure.

(iv) Modulation of expression, preferably by use of antisense RNA to block expression, of critical target genes/ IG's, such as the mcrA, lit, pin, ykgM and ykgk genes.

(v) Evaluation of compounds for the ability to modulate expression of target genes, such as mcrA, lit, pin, ykgM and ykgk, or to inhibit or enhance activity of the encoded protein products.

Specific Bacterial Populations

We envision that control of persister state in bacteria may be accomplished in multiple bacterial populations, although the Examples below are specific to *E. coli*. When we did GeneBank searches of the IG sequences we noted significant homology across a wide range of Gram-positive and Gram-negative bacteria. This implies that the IG's are not only conserved within *E. coli* but that they represent regulatory systems that evolved very early in prokaryotic lines.

Many sequenced bacterial genomes harbour phage-like elements or cryptic prophages. These elements have been implicated in pathogenesis, serotype conversion and phage immunity. The e14 element is a defective lambdoid prophage element present at 25 minutes in the *E. coli* K-12 genome. This prophage encodes important functional genes such as lit (T4 exclusion), mcrA (modified cytosine restriction activity) and pin (recombinase).

In the Examples below, we have demonstrated alteration of persister function in *E. coli* by altering expression of the mcrA, lit, pin, ykgM and ykgK genes. We believe that alteration of corresponding genes in other bacterial species would be successful. By "corresponding genes" we mean greater than 20 nucleotides homology preferably analyzed in a BLAST search. By genes specifically corresponding to mcrA, lit, pin, ykgM and ykgK genes, we mean the species disclosed in Table 17 to be preferable examples.

Control of Persister Status

Persistence is a phenotype enjoyed by a small fraction (<1%) of any population of bacteria. These persisters determine the overall treatment strategies required to treat/cure infections and to render a surface or product hygienically clean. In microbial biofilms the level of persistence is increased and the populations enjoy other mechanisms by which they become collectively less susceptible towards inimical treatments. Methods of the invention, therefore, offer the potential to eliminate persisters within populations of bacteria in both planktonic mode and growing as biofilm through interaction at implicated target sites/DNA/RNA.

In the context of antibiotic therapy such advantages of the invention would not only reduce the amounts of antibiotics necessary to treat many infections but might also render effective many of those antibiotics that have become ineffective through resistance development. This is because persistence and conventional resistance mechanisms are complimentary rather than synonymous. Antibiotic effectiveness is determined by the susceptibility of the least susceptible phenotype within an infecting population of bacteria. In the treatment of antibiotic sensitive infections then the least susceptible cells are the persisters. In the event of treating antibiotic resistant populations then it is often the resistant-persister co-phenotypes within this infection that drive therapeutic failure. Elimination of the persister phenotype, even within populations of bacteria that have developed resistance, will provide some redress and render effective many currently disused antibiotics. The invention therefore offers potential synergists to antibiotic formulations.

The present invention, therefore, offers the advantages of increased efficacy of biocides, reduced environmental load, and reduced treatment times (i.e. tuberculosis). For example, breaking of persistence might provide a means of activating populations of soil bacteria associated with fouled land. Such activation would lead to a more rapid establishment of biodegradative partnership/climax communities.

Since hygienic formulations must typically be capable of generating 5 log of kill within five minutes exposure, then it is the susceptibility of the subset of persisters (0.1-1%) that determines the concentration of active biocide that must be deployed. Rapid reversal of persister cells to normal cells would therefore dramatically reduce the concentrations of active biocide required. This would not only increase the profitability of the product but also would co-incidentally reduce the environmental challenge of biocide use. Biocides affected would include all except the strongly oxidising biocides such as hypochlorite and peroxides.

The invention also offers the potential to induce persistence in a target population. This has clear implications in the area of preservation such as in biomaterials-preservation, cosmetics, foods, anti-corrosion, etc., where the preservative is intended to prevent the growth of unwanted microorganisms rather than to kill them. Induction of persistence/quiescence is unlikely to result in the selection of resistance because of the lack of metabolism, transcription and DNA replication.

Similar induction of persistence/quiescence might find application in the personal products industry for the control of malodor in the mouth or axillae, and in the control of fouling of oil-fields, which is through $H_2S$ and $SO_2$ production by disulphobacteria.

In light of the discussion above, in one embodiment the present invention is a method of controlling or modulating persister status in a bacterial cell population comprising the step of increasing or decreasing the expression of native chromosomal sequences or enhancing or suppressing the product of particular native gene sequences. By "control" or "modulation" of persister levels, we mean that one may render the cell population non-persistent, decrease the percentage of persister cells, or may stabilize or increase the persister status for particular applications. A change of persister levels of at least 10%, preferably 30%, is "modulation" of persister levels.

Preferable methods for analyzing persister status are noted in the Methods section. Typically, the change in persister status for a single persister cell is measured by the cell becoming susceptible to a treatment that previously it would have survived. In a population of bacteria change in persister status is reflected in a reduction in the proportion of the cells within the target population that express this phenotype. Typically, for a population we would see this as a change in survival kinetics from a time survival curve which plateaus (persisters represent the plateau) to one that truly obeys first order kinetics.

The level of persisters in a population increases particularly in stationary phase. Demonstration of elimination of persister cells in stationary phase is therefore a better demonstration of phenotype modification than when done in logarithmic phase.

Specific Genetic Targets

Listed below are particular native chromosomal sequence targets that we believe will accomplish the goals described above. We have listed below the target, the location of the target on the E. coli chromosome, and our predictions regarding persister behaviour when expression of the target sequence is modified.

Modulating the Expression of Genetic Targets

By "modulating the expression" of genetic targets, we mean that one may wish to either increase or decrease the expression of the native chromosomal targets described in Table 8, depending on whether one wishes to decrease persister status in the bacterial population or stabilize or increase the status. The targets described above may be modified by many methods known to one of skill in the art in molecular biology. Preferably, one would wish to modify expression of mcrA, lit, pin, ykgM or ykgK or bacterial genes corresponding to mcrA, lit, pin ykgM or ykgK.

For example, one may wish to use antisense RNA strategies to inhibit the expression of a chromosomal area or interaction of that chromosomal area with other cellular components. Antisense strategies for gene silencing, employ antisense RNA that binds to and inhibits a target RNA. Nucleic acid-based molecules (Good, L., Cell. Mol. Life Sci. 60:854-861, 2003) and, more recently, the discovery of RNA interference (RNAi) (Ji, Y., et al., Science 293:2266-2269, 2001) offer additional approaches for regulating gene expression. These methods typically require sequence-specific design and have proved valuable in post-transcriptional gene silencing. Such approaches will be of particular application where the desired effect can be achieved by decreased expression of a particular DNA sequence (i.e. preferably lit, pin, mcrA, ykgK, ykgM).

Additionally, one may wish to supply inhibitors or enhancers of gene products. For example, with respect to the anti-toxin/toxin pairs, clearly the anti-toxin is the inhibitor of the toxin. If these gene products are identified as candidate targets then further work would be conducted involving overexpression of the product, crystallography, fine structure and then computer based design of specific inhibitors, probably through a combinatorial chemistry approach and high throughput screen. This is standard practice in the art once a protein target has been identified. For those target genes that encode translatable RNA, and thereby protein, the protein product becomes a valid target amenable to conventional approaches of rational drug design through (i) overproduction of the protein, (ii) determination of crystal structure through X-Ray crystallography and (iii) de-novo design of small chemical inhibitors. Table 15 discloses a correlation between increase or decrease of persister levels and increase or decrease in gene expression of particular genes. One would consult Table 15 if one wished a particular result. For example, if one wished to decrease persister levels, one may wish to inhibit ykgK gene expression.

In another embodiment of the present invention, one would wish to reduce or increase the expression of native chromosomal sequences within E. coli regions 287628-365529 and 1196090-121226. These are "hot spot" regions for persister regulation. Preferably, one would reduce or increase the expression of sequences by the following manner: Within each of these "hot-spot" regions there are putative regulations of various classes (i.e., Table 3 discloses yagP, ykgA, betI, yahB, yahH, prpR and cynR). These regulators most probably moderate the expression of adjacent regions/operons. The next phase of work will examine the effects of knockout/nullification by an antisense approach. For each validated as a target then the intention would be to screen for inhibitors/blocking agents by the same strategy as indicated above (i.e. characterization of the gene product, de-novo design of potential inhibitors and or combinatorial chemistry/high throughput screening for agonists/antagonists. We feel it important to be leading the work through to small chemical inhibitors/blockers of persistence for cheapness and simplicity. Antisense RNA strategies (as above) could also be deployed to block the regulators more specifically.

Additionally, one may wish to provide an increase or decrease in expression of particular targeted genes. This may best be done by moderating the expression in populations by the supply of the antisense in the form of a plasmid. It would work well where we were deliberately trying to induce persistence (i.e. in biofermentation) in such an instance the plasmid would be made conditional (i.e. temperature or amino acid conditional) so that the population biomass could be maximized before persistence was induced in all the population.

Identification of Compounds

As described above, in a treatment mode one would wish to identify relatively small molecules that can be cheaply produced and easily delivered into a bacterial population/biofilm (above). Preferably, these molecules would alter the expression of mcrA, lit, pin, ykgM or ykgK or bacterial genes corresponding to these genes. The molecules may also inhibit or enhance gene products.

One might identify suitable small molecules in various manners: Our approach with the target validation using conditional antisense RNA was that the antisense RNA will bind to the naturally produced RNA neutralizing it and preventing translation/operation as an ncrRNA. Where the target has the potential to be translated to a protein, then it is that protein that carries the biological function. Design of inhibitors could either be directed at the level of RNA or the translated protein. One might expose a library of test compounds to *E. coli* and measure expression of a target gene at either the RNA or protein level. One could expose test compounds to preparations of protein products and measure inhibition or enhancement of protein function.

EXAMPLES

1. In General

We have developed a method, using a fluorescent reporter gene, flow cytometry and fluorescence activated cell sorting, which enables the separation of persister cells from standard cultures prior to exposure to antimicrobials. Persisters can be harvested in sufficient number so as to facilitate DNA microexpression array analysis. In the absence of antimicrobial stress, then patterns of gene expression were substantially different from those in the Keren, et al., (supra, 2004) study suggesting that the relative expression of relE and hipA are responses to antimicrobial treatments rather than pre-determinants of persister status.

Levels of mRNA expression in spontaneous persisters populations were less than 1% of that of the bulk population. This suggested that quiescence and adoption of a dormant vegetative state underlies the persistence phenomenon.

Of the 22 most upregulated, 17 regions corresponded to intergenic regions, defined as non-coding sequences between ORFs (open reading frames). Some of these intergenic regions were several thousand nucleotides in length and could relate to uncharacterised ORFs or may act as gene regulatory regions and include binding sites for regulatory proteins (Blattner, et al., *Science* 277:1453-1462, 1997). These included IG201, IG199, IG197, IG186, IG870 and IG205. All of these, with the exception of IG870, were adjacent to heavily upregulated ORFs. One may correlate these numbers with sequence data by reference to the NCBI *E. coli* database. When mapping these intergenic regions together with their adjacent genes and ORFs it was observed that they all fell within a contiguous region of the chromosome, from nucleotide position 287628-365529, most of which was heavily upregulated. This region includes the CP4-6 prophage ORFs associated with, among other things, a toxin-antitoxin protein pair and a number of transcriptional regulators corresponding to the ARAC (ykgA, ykgD, icIR, yagl) and LysR (yagP, yahB) families.

IG747 is also large but now recognized to contain a large number of e14 prophage genes the majority of which are upregulated. Included here are both positive and negative regulators (downregulated) of lit, pin and mcrA. All of these are upregulated in the persister phenotype. mcrA is among the top 20 most highly expressed regions of the array. Interestingly, the upregulated region associated with IG747 includes not only mcrA but also stfE and IG754. The latter is a small intergenic region 106 nt in length and appears within the top 20 upregulated regions and is adjacent to a downregulated transcriptional regulator of the merR Family. merR regulators have been shown to activate sub-optimal sigma(70)-dependent promoters. Both Sigma 70 and Sigma E are both heavily down-regulated in the array. Lit is of particular interest in that it encodes for a T4 phage head protein that acts as a universal repressor of translation. This is a particularly strong candidate for a quiescence mechanisms/switch.

Sequence analysis of the remaining upregulated intergenic regions revealed that all except for IG1604 contained one or more YUNR-motifs within hairpin loops of the secondary RNA structure. This strongly suggests that they are non-coding, regulatory RNA and as such, are able to regulate gene expression. Putative insertional knockouts were constructed for six of the nine smaller intergenic regions, and IG870, all of which were associated with profound changes in persister phenotype as detected through exposure to quaternary ammonium biocides.

BLAST (Basic Local Alignment Search Tool) (Altschul, et al., *J. Mole. Biol.* 3:403-410, 1990) analysis of the upregulated intergenic regions against the *Escherichia coli* K12 genome showed that many contained significant (>95%) homology (20-100 bp) with other upregulated intergenic regions, and neighbouring intergenic regions (secondary intergenic regions). In several instances secondary intergenic regions were associated with strongly up-, or downregulated genes and gene families, and some showed sequence homology to more than one primary intergenic region. In most cases the sequence homology was between YUNR-motifs on open hairpin loops. Significant (94%) homology was shown between the upregulated IG873 (18 nt (nt=nucleotide)) and ykgM, also within the highly expressed genes.

We conclude that cells are maintained in a persister state through physiologies mediated by regulation of the e14 and CP4-6 prophage assemblies, possibly involving toxin:antitoxin pairs of proteins, together with a cascade of non-coding, regulatory RNAs that globally regulate metabolism. Under such suppression, the majority of mRNA degrades and the cells enter a quiescent state in which they become tolerant of inimical chemical stress. Such regulatory systems offer potential targets through which persistence might be moderated either to activate the cells and render them antibiotic sensitive (persisticide) or to induce quiescence as a form of population control.

Of the identified 12 target genes (described below), it was possible to generate conditional mutants that overexpress and/or suppress through production of antisense RNA to six of these. 10 mutant lines were constructed altogether, where four pairs enabled the switching up and suppression of single target genes (lit, pin, ykgK and ykgM), the remaining two constructs enabled the overexpression of mcrA and yagL. The generated mutant library therefore give total or partial coverage of half of the initial primary targets. Of these, the phenotypes were profoundly altered with respect to persistence by overexpression/antisense suppression in 5/6 targeted genes.

The present study identifies a number of potential mechanisms by which *E. coli* regulates gene expression in persister cells and "choose" to survive. One such potential mechanism of regulation is phase variation, mediated through expression of persister genes reported here, through mcrA (Table 15). Phase variation is the process whereby bacteria undergo reversible on/off switching of gene expression, and is paralleled by the temporary expression of a persister cell state. Located within the e14 prophage region of *E. coli*, mcrA encodes the 5-methylcytosine-specific restriction endonuclease B protein, responsible for restriction of DNA at 5-methylcytosine residues. Restriction-modification systems in a number of bacterial pathogens are subjected to phase variation. Srikhanta, et al., (*PNAS* 102, 5547-5551, 2005) recently demonstrated a phase variable global regulatory role for a type III restriction-modification system in *Haemophilus influenzae* and hypothesized that phase variation may be a frequently used mechanism for the multiple control of genes in other bacteria. Interestingly, Srikhanta, et al. (supra, 2005) also find that the phase variable regulation of the type III restriction-modification system in *Haemophilus influenzae* influences the expression of multiple genes with common functions (heat shock proteins). This could be similar to mcrA, where the expression of this gene is involved in the global control of other persister genes.

2. Materials and Methods

Organism and Maintenance

*Escherichia coli* K-12 C600 was obtained from Dr. Michael Kertez at the University of Manchester (Manchester, UK). We introduced the mini-Tn5 transposon derivative mTn5gusA-pgfp21 (Xi, et al., *J. Microbiol. Meth.* 35:85-92, 1999) into a general housekeeping region of the *E. coli* K-12 C600 chromosome by electroporation (Sambrook and Russell, "Molecular Cloning—A Laboratory Manual," 3rd Ed., Cold Spring Harbour laboratory Press, New York, USA, 2001), conferring constitutive GFP fluorescence to the bacterium. gfp (green fluorescent protein) expressing colonies could be visualized on agar plates under UV illumination. Incorporation of the gene encoding GFP by transposon mutagenesis into the chromosome meant that antibiotics and other selective agents were not required for maintenance. *E. coli* K-12 C600 and the gfp expressing strain *E. coli* K-12 C600::mTn5gusA-pgfp21 were maintained on nutrient agar (Oxoid, Hampshire, UK) at room temperature in a darkened cupboard after overnight incubation at 37° C. Long-term storage of all strains was achieved using the Protect™ bacterial preservation system and cultures were stored at –60° C.

Growth in Liquid Culture

Liquid cultures were produced in nutrient broth (Oxoid). Approximately 4-5 colonies were used to inoculate a 250 ml conical flask containing 100 ml of a nutrient broth. Cultures were incubated (16-18 hours) at 37° C. in an orbital shaker at 200 rpm (G24 environmental incubator shaker, New Brunswick Scientific Co. Inc., New Jersey, USA). Such stationary phase cultures were either used directly in subsequent experiments or used as starter cultures whereby 2 ml of the culture was inoculated into a fresh 100 ml of nutrient broth and incubated as described above unit mid exponential phase (OD, $E_{470nm}$ of 0.8) was achieved (approximately 3.25 hours), as assessed by optical density measurements at 470 nm.

Susceptibility to Antibiotics and Biocides

Time-dependent survival experiments were performed following exposure to various antibiotics and antibacterials by mixing either stationary phase cultures (3.68 µg/mL Tetradecylbenzalkonium chloride used for stationary phase cultures) or mid-log phase cultures with fresh solutions of biocidal agent (0.75 µg/mL amikacin; 0.7 mg/mL bacitracin; 0.5 µg/mL cetrimide USP (United States Pharmacopeia), 0.05 µg/mL ciprofloxacin, 40 µg/mL tetracycline) to give $1 \times 10^4$ cfu/mL and $1 \times 10^{10}$ cfu/mL respectively. In the latter set of experiments reaction mixtures included nutrient broth (25% normal strength) in order to facilitate growth during the exposure. This was necessary in order to get adequate killing by β-lactam antibiotics. At various time intervals samples (0.1 mL) were removed and serially diluted either in sterile phosphate buffered saline (pH 7, 0.1M) or lecithin (2% w/v)—tween 80 (3% w/v) broth as a specific neutralizer of quaternary ammonium biocides (Wright, et al., *J. App. Bacteriol.* 62:309-314, 1986). Samples of appropriate dilutions were plated, in triplicate, onto nutrient agar and colonies counted after 16 hour incubation at 37° C. Survival was expressed relative to untreated control suspensions.

Flow Cytometry and Cell Sorting

During the course of this work, flow cytometry and cell sorting was utilized to characterize the patterns of fluorescence in target communities and to separate relatively small numbers of live cells (circa $10^5$ cfu) for subsequent analysis of growth patterns and susceptibility towards antimicrobials. For this purpose a Fluorescent Activated Cell Sorter (FACS) Vantage Flow cytometer was deployed (BD Biosciences, Oxford, UK). The sort rate for the FACS Vantage (3000 sorts/s) was adequate to separate small fractions of the populations when the target number of cells was less than $10^5$ (circa 10 min collection time), but was inadequate for the generation of materials for DNA microarray analysis where circa $10^9$ cells were required. Using the FACS Vantage this would have entailed sorting experiments of >500 hours duration. In order to accommodate the isolation of cells for microarray analysis a faster instrument was required. The fastest machine available is the MoFlo Flow Cytometer and Sorter (DakoCytomation, Ely, UK) which can conduct up to 70,000 sorts per second. Nevertheless, separation runs of 32 hours were required to prepare materials for array analysis even using this machine. Given this extended separation time then measures needed to be adopted to prevent RNA degradation and to ensure homogeneity of the input culture. The two approaches are described below.

Flow cytometry using the FACS Vantage: The gfp expression profile of cells within stationary phase and mid-log phase cultures of the gfp expressing *E. coli* K-12 C600::mTn5gusA-pgfp21 was determined using the FACS Vantage flow cytometer (BD Biosciences, Oxford, UK). Volumes (20 mL) of either mid-exponential or stationary phase cultures were harvested by centrifugation (10,000 x g, 10 min) using the Sorvall® RT6000 refrigerated centrifuge (Sorvall, Conn., USA). Pellets were washed three times in PBS (Phosphate Buffered Saline) (20 mL) before passing through the cytometer. The LinearFlow™ Green Flow Cytometry Intensity Calibration Kit (Molecular Probes, Introgen Detection Technologies, Paisley, UK) was used for calibration. Distributions of fluorescence intensity within populations was based on a minimum observation of 20,000 cells as detected by side scattered light. Data generated was analyzed by the software package CELLQuest version 3.

When cells were required for culture and/or susceptibility determinations collections were made of discrete fractions of cells within the upper 1 and 5%, and the lower 1, 5 and 10% of fluorescence intensity. Control populations consisted of the entire population of cells having been passed through the cytometer and sorter. Cell sort rates of circa $10^3$/sec were deployed enabling collection of circa $10^{4-5}$ cfu within 10 minutes. Cell concentrations were adjusted from the cytometer count by dilution with fresh PBS. Suspensions of collected cells were used immediately for microbiological analysis.

Flow cytometry using the MoFlo Cytometer and Sorter: The relatively slow sorting rate associated with the FACS Vantage flow cytometer negated its use for the preparation of cells for microarray analysis. A faster machine was deployed. The MoFlo flow cytometer (DacoCytomation, Ely, UK) is the fastest cell sorter currently available on the market and was able to sort the 5% of the cell population at a rate of circa 3500 cells per second. Initial studies confirmed that distributions of fluorescence intensity within the *E. coli* K-12 C600::mTn5gusA-pgfp21 cultures replicated that shown with the FACS Vantage. Fluorescence intensity distributions were, in this instance, generated using the Summit software package (ver. 3.1; Cytomation, Inc., Fort Collins, Conn.).

The numbers of cells required for extraction of RNA and subsequent DNA microarray analysis is circa $10^9$. Even with the fast sort rates obtainable with the MoFlo this required extended separation runs. Preliminary experiments were conducted analyzing the susceptibility characteristics of the lower 5% of cells according to their fluorescence intensity at various times after being harvested from their stationary phase of growth. Such experiments indicated that the persister status of these separated cells did not change from 1 hour into stationary phase during centrifugation and following 4 hours storage in PBS. Accordingly for the sorting experiments replicate cultures of *E. coli* K-12 C600::mTn5gusA-pgfp21 were inoculated at 2 hour intervals and monitored through to stationary phase by optical density measurements. One hour after achieving stationary phase they were harvested by centrifugation (10,000 x g 10 min), washed and resuspended in PBS. These suspensions were transferred directly to the MoFlo cytometer and sorter and sorted for a 2 hour period. The presence of cells was detected by forward light scatter and fluorescence detected on the side-scatter. At the end of each 2 hour period the input suspensions was changed for a fresh one. Each 2 hour sort experiment collected the lower 5% of fluorescence intensity cells for the majority of the time but at its mid-point was recalibrated to collect the upper 75% of fluorescence intensity cells for circa 20 minutes. Collections of sorted cells were made directly into tubes containing 5 mL of RNA Protect (neat) (Qiagen, Hilden, Germany) until the tubes contained a total of 50 mL. Based upon the sort rates of MoFlo flow cytometer, a minimum of 8 consecutive batch cultures of the gfp expression *E. coli* K-12 C600 was required to isolate sufficient quantities of persister cells for microarray analysis, making the total sort time 16 hour. Two replicate separation runs of 16 hour were conducted. All collected fractions were bulked, subjected to freeze-drying and the resultant lyophilate was resuspended in a reduced volume of RNase and DNase free water (Sigma, Dorset, UK) and subjected to RNA extraction (below).

RNA Extraction and Quantification

The total RNA of the separated lyophilized fractions was extracted using an RNeasy RNA isolation kit (Qiagen, Hilden, Germany) following the manufacturer's instructions. RNA quantification was achieved with a NanoDrop ND 1000 UV Vis Spectrometer (NanoDrop Technologies, Montchanin, Del., USA) calibrated against standards.

DNA Expression Arrays

Affymetrix GeneChip® *E. coli* Antisense Genome Arrays (Affymetrix UK Limited, High Wycombe, UK) were used to analyze the gene expression profile of the lower 5% of fluorescence intensity cells compared to control samples corresponding to the upper 75% collected at the midpoints of each separation run. Briefly, the Antisense Genome Array contains probe-sets for over 4200 ORFs and over 1350 intergenic regions. The sequence information for probes on this array corresponds to the K-12 derivative M54 of the *E. coli* K-12 Genome Project database at the University of Wisconsin. Microarray experiments were performed at the Affymetrix Department in the University of Manchester. Duplicate samples of persister cells (0-5% fluorescence intensity) and control samples (25-100% fluorescence intensity) were analyzed. Background correction and normalization was carried out using RMAEXPRESS (Bolstad, et al., Bioinformatics 19, 185-193, 2003). Correlation analysis was achieved with MAXDVIEW (available from http://www.bioinf.man.ac.uk/microarray/maxd/).

Bioinformatics

RNA secondary structure determination: RNA sequences of each intergenic region were derived from DNA sequences in the sense orientation using the Sequence Editor website. The MFOLD web server for nucleic acid folding and hybridization prediction, available on the world wide web, was used to generate hypothetical secondary structures. Where more than one hypothetical secondary RNA structure was generated, only the most probable structure is discussed here. BLAST searches and sequence alignment: Chromosomal positions of the upregulated intergenic regions were obtained from the Affymetrix website. The nucleotide sequence for the complete genome of [1]*E. coli* K-12 (NCBI gene bank number UC00096, NCBI reference sequence NC_000913.2) was accessed via the NCBI website.

Generation of Knockout Phenotypes

Intergenic knockouts were made to *E. coli* K-12 C600::mTn5gusA-pgfp21 with respect to IG216, IG477, IG870, IG873, IG1602, IG1604 and IG1484 using the protocol described by Datsenko, et al. (*Proceedings of the National Academy of Sciences of the United States of America* 97, 6640-6645, 2000). Plasmid pKD3 was used as a template to generate PCR products with a selectable antibiotic resistance marker (chloramphenicol) and 40 nt homology extensions relating the genes flanking each targeted intergenic region. Modifications of the method included a 10-fold increase in the concentration of L-arabinose (10 mM) for induction of λ Red genes in the helper plasmid pKD46, and 50-fold increases in the amount of PCR product (500 ng) used to transform *E. coli* K-12 C600 containing pKD46. Further amendments to the method were associated with recovery of transformants following electroporation. In addition to selecting for transformants as described by the authors on LB (Luri-Betrani) agar plates containing 25 μg/ml chloramphenicol following recovery of electroporated cells in chilled SOC medium, agar plates containing 2, 5 and 10 μg/ml chloramphenicol were also used. Furthermore, transformants were also enriched in LB broth in 2, 5, 10 and 25 μg/ml chloramphenicol and in the absence of chloramphenicol for 24 and 48 hours at 37° C. at 200 rpm in an orbital shaker. Following incubation, transformants were selected on LB agar containing 25 μg/ml chloramphenicol.

Susceptibility of Putative Knockouts towards Cetrimide USP

Putative intergenic knockouts were grown as liquid culture in nutrient broth, harvested at mid-exponential phase, washed in PBS as described in section 2.1 (a) and adjusted to $1 \times 10^5$ cfu/ml in PBS. Cells were exposed to 0.6 and 2.0 μg/ml cetrimide USP for 1 hour in 25% nutrient broth with final concentration of $5 \times 10^4$ cells/ml. Control tubes without the addition of the biocide containing the same concentration of cells and nutrient broth were always run in parallel. The viability of cells in the antimicrobial and control tubes was monitored after 1 hour incubation at 37° C. at 200 rpm in an orbital shaker. Survival was expressed relative to untreated control samples. The susceptibility of the mother strain *E. coli* K-12 C600 towards cetrimide USP was investigated in the same experiments and was used as a reference to determine the affect of replacement of each target intergenic region with the chloramphenicol resistance marker.

3. Results

Persistence Status and Heterogeneity of Fluorescence Intensity

Distributions of fluorescence intensity within stationary phase, and exponential phase, nutrient broth grown cultures of *E. coli* K-12 C600::mTn5gusA-pgfp21 were determined using the FACS Vantage cytometer. In all instances fluorescence intensity, illustrated in FIG. 1. for stationary phase cultures, approximated to a normal distribution with extreme intensities (expressed as levels of FITC fluorescence intensity) varying within the population by 100-fold. Collections of discrete populations of cells corresponding to the lower 5% of fluorescence intensity were made and the cells sub-cultured overnight in fresh nutrient broth. On each occasion collections of poorly fluorescent cells re-generated the parent population of fluorescence distribution (FIG. 2). The selection and re-growth was performed for fifteen consecutive passages without change in the parental fluorescence distribution curve.

Antimicrobial Susceptibility of Persister Cells

Figure 2:
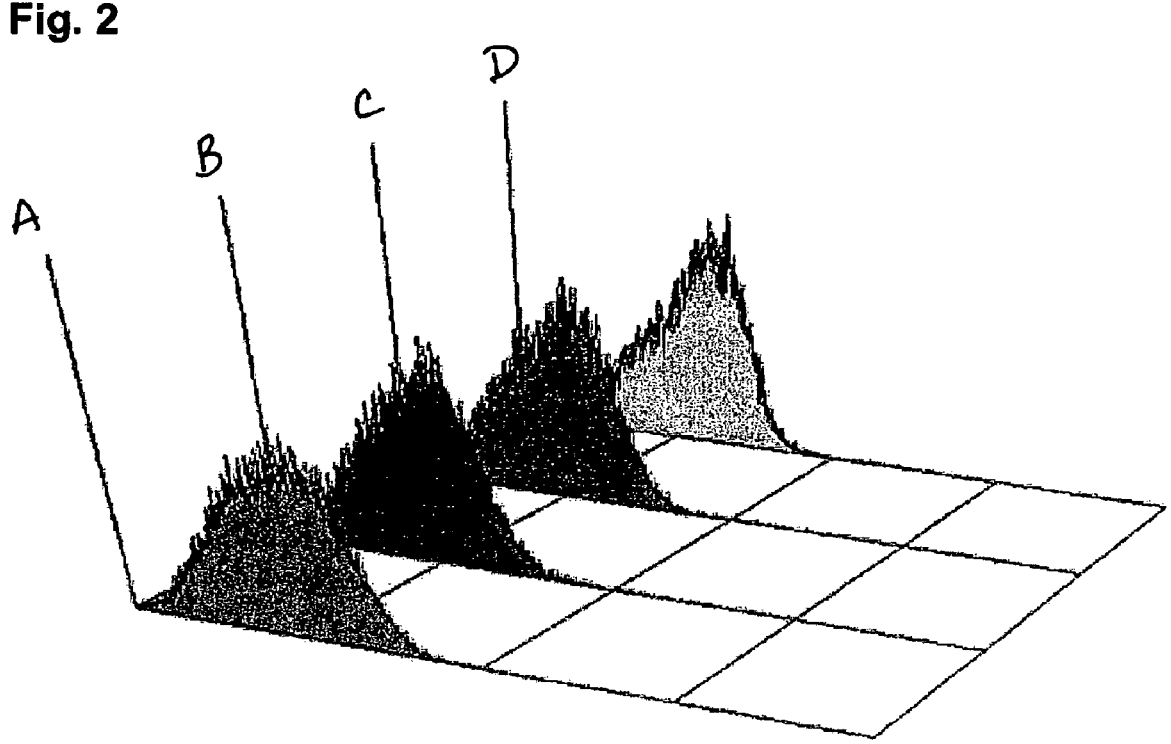
FIG. 2. Distributions of fluorescence intensity distribution in stationary phase cultures of E. coli K-12 C600::mTn5gusA-pgfp21 inoculated into nutrient broth at 37° C. with low fluorescence intensity cells collected by live cell sorts using a FACS vantage flow cytometer. The different curves correspond to cultures passaged by cell sorting and subsequent batch culture on a single occasion (A) and after five (B), ten (C) and fifteen passages (D).
Figure 3:
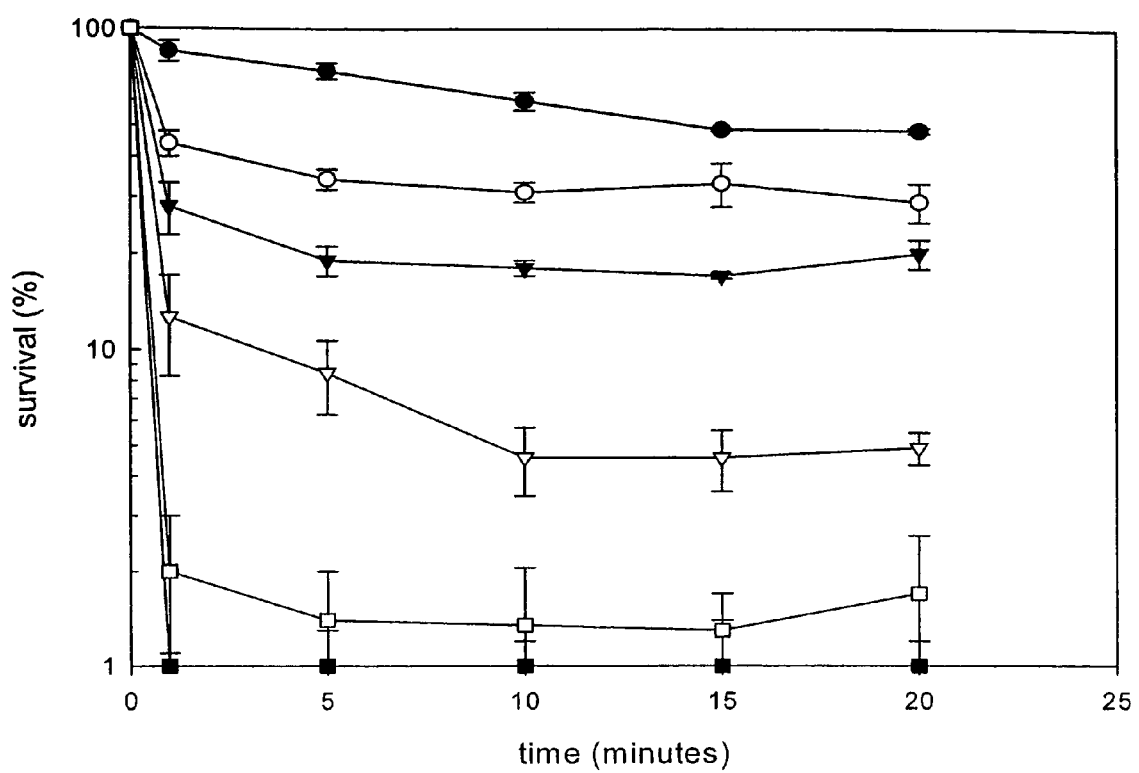
FIG. 3. Time-dependent survival of E. coli K-12 C600::mTn5gusA-pgfp21 following exposure to tetradecylbenzalkoium chloride (3.68 mg/mL) at room temperature. Inocula were separated from stationary phase nutrient broth cultures by FACS Vantage cytometer according to their fluorescence intensity. Fluorescence Intensity (0-1%, ♦; 0-5%, ○; 0-10%, ▲; 95-100%, □; 99-100%, ■; whole population, △).

The FACS vantage was also deployed to separate populations of cells, from stationary phase cultures, corresponding to the lower (1, 5 and 10%) fluorescence intensity cells and the upper (1 and 5%) fluorescence intensity cells (FIG. 1). These cells were immediately subjected to exposure to tetradecyl-benzalkonium chloride (3.68 μg/mL) for various times up to 20 minutes. After neutralization in lecithin-tween 80 broth the numbers of surviving cells was determined by plate count. Results are shown in FIG. 3. In all instances the shapes of the survival curves were non-linear indicating an initial rapid phase of killing followed by a plateau phase. Previous work (Sufya, et al., supra, 2003) had demonstrated that, at these concentrations of biocide, the plateaus did not correspond to capacitative consumption of the antimicrobials. Survival beyond 10 minutes exposure therefore reflected the presence of non-susceptible cells. Importantly, the data show that the proportion of persister cells within the parent population was related to fluorescence intensity, whereby the least intensely fluorescent cell fraction (1%) contained >80% of persister cells. The most fluorescently intense cells, indicating the most metabolically active, were eradicated beyond detection after 1 minute exposure to the same concentration of benzalkonium chloride. The control, corresponding to the complete population after passage through the cell sorter demonstrated an intermediate level of susceptibility and presence of persisters.

Collections of poorly fluorescent cells from mid-log phase cultures were made and susceptibility re-determined towards tetradecylbenzalkonium chloride, and towards various other treatment agents. The proportion of persisters to tetradecylbenzalkonium chloride was substantially reduced in mid-log phase from that in stationary phase supporting the view that persister status related to growth rate and metabolic activity. Susceptibility towards amikacin (0.75 μg/ml), bacitracin (0.5 μg/ml), cetrimide (0.5 μg/mL), ciprofloxacin (0.05 μg/mL) and tetracycline (40 μg/mL) was determined by exposure over a period of 1 hour at 37° C. Results are presented in Table 1 and show lack of susceptibility towards the quaternary ammonium biocides within the poorly fluorescent sub-set of cells to be paralleled by an equal lack of susceptibility towards these other agents.

Persister Status, RNA Transcription and Genomic Expression Patterns

To separate cells for DNA microarray analysis the donor culture was grown to stationary phase to maximize the level of persisters. Collections of cells were made for analysis that corresponded to the least intensely fluorescent cells (0-5% and 0-8%), the lower half of the fluorescence distribution (0-50%) mid-range (25-75%) and the whole donor culture (0-100%). Extraction and quantification of the amounts of RNA per unit cell mass indicated that the levels of RNA expression in the cells having the least fluorescent intensity was less than 1% (0.72 μg/$10^8$ cells) of the parent population (51.2 μg/$10^8$ cells) with amounts of RNA per cells being significantly reduced in the 0-8% (2.74 μg/$10^8$ cells) fluorescence intensity band. Levels of RNA expression supported the view that the persister cells were relatively slow growing or dormant.

Levels of RNA extracted were sufficient to develop DNA expression arrays. Data is presented in FIG. 4 in the form of a plot relating the expression of all ORFs and intergenic regions represented on the chip averaging the expression of the control population (upper 75% of fluorescently intense cells) and relating it to the expression level demonstrated by the least fluorescently intense set of cells (0-5%). The majority of detected spots were equally expressed in the two cell fractions and fall on a diagonal line bisecting the plot. Deviation by more than a factor of two from this line of equivalence is significant and indicates differential expression between the two cell types. Interestingly, there was little or no detectable expression of RNA in the lower 0-5% fraction for circa 40% of ORFs whereas this figure was reduced to ~14% of ORFs for the lower 0-8% fraction with less than 3% of ORFs being at the limit of detection in the control cell population. Once again this indicated that metabolic activity, reflected in RNA transcription, was suppressed in the persister sub-set of cells, and led us to examine upregulated genes and sequences rather than downregulated ones.

Figure 4:
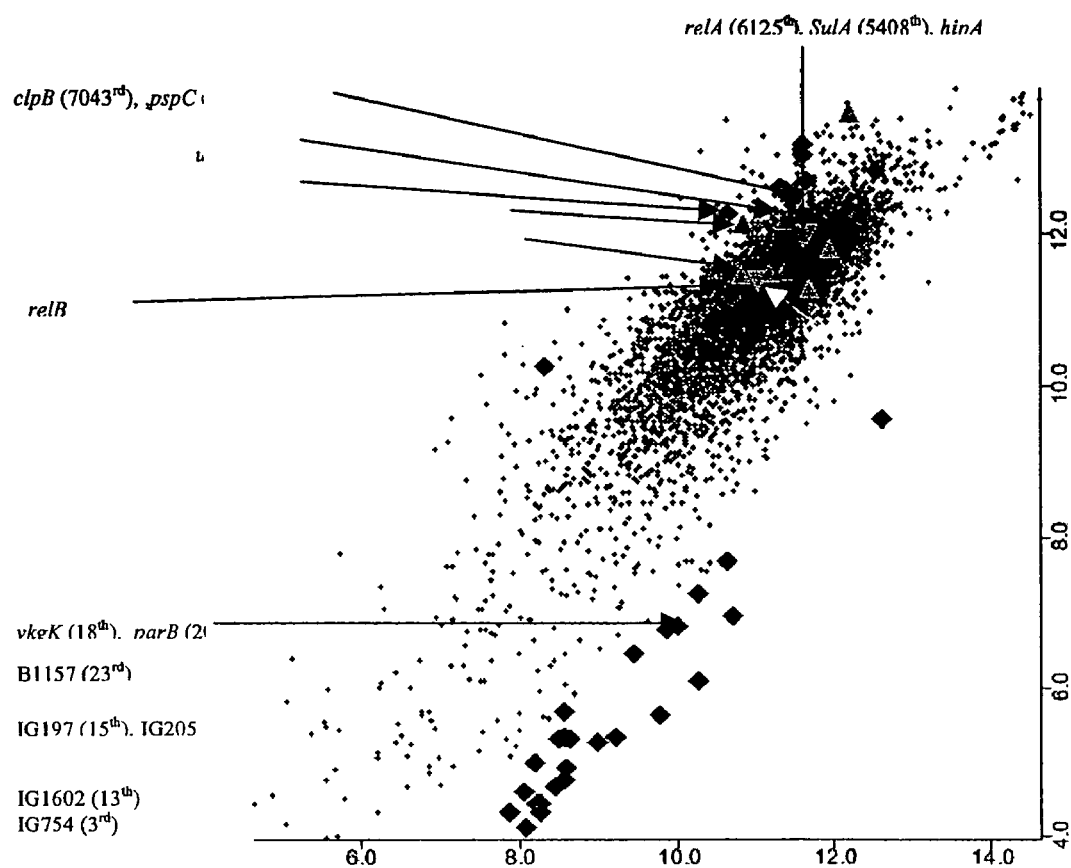
FIG. 4. RNA expression profile of persister cells (lower 0-5% of fluorescence intensity) compared to controls (25-100% of fluorescence intensity). Each point on the graph corresponds to a single orf. Upregulated orfs associated with the persisters are indicated by ♦. Other marked genes correspond to the upregulated "persister-genes" reported by Keren, et al., (supra, 2004) and Babalan, et al., (supra, 2004). Phage shock genes, ▽; SOS response genes (○); toxin-antitoxin TA genes (●); stringent response genes (△).

The developed DNA expression arrays indicated a set of approximately 20 ORFs that were highly expressed in the persister cells irrespective of the overall suppression of RNA transcription. Interestingly rather than correspond to the most highly expressed ORFs reported in the Keren, et al., (supra, 2004) study these corresponded mainly to intergenic regions (17 out of 22). Significantly, as indicated in FIG. 4, the upregulated ORFs from the Keren, et al., (supra, 2004) study were downregulated in these spontaneously generated persister cells. The most upregulated intergenic regions are listed in Table 2 together with their expression level, size and description of up- and downstream ORFs.

Bioinformatic Analysis

Ten of the upregulated IG regions corresponded to small intergenic regions between 30 and 300 nucleotides in length. The remaining seven were large and subsequently found to have been partially reassigned in the *E. coli* genome to newly designated ORFs and genes. The majority of these were associated with heavily upregulated regions of the chromosome and are discussed below. All showed some unusual degree of homology within themselves, adjacent genes and with remote secondary intergenic regions. These homologous regions were not in hot spots of up-regulation rather the secondary intergenic regions showed high levels of homology with a further set of intergenic regions (tertiary) that were variously associated with both upregulated and downregulated gene sets. This bioinformatic analysis will therefore consider separately the (i) secondary RNA structure of the classical IG regions, (ii) patterns of genomic expression around the most expressed ORFs/putative IG regions, (iii) homologies between primary and secondary intergenic regions and (iv) expression levels in regions associated with homologous secondary and tertiary intergenic regions.

(i) Secondary RNA Structure

Sequence analysis of the upregulated intergenic regions revealed the presence of YUNR-motifs (pyrimidine-U-N-purine) (Franch, et al., *J. Mole. Biol.* 294:26572-26578, 1999) in all, bar one, upregulated intergenic region (IG1604). The presence of YUNR-motifs within loops are implicated in promoting the initial interaction between regulatory RNA and its target DNA in plasmid and phage systems (Franch, et al., supra, 1999) and it has been suggested that this phenomenon may be extended to the less well understood chromosomal regulatory RNAs (Gottesman, *Genes Dev.* 16:2829-2842, 2002). Most probable secondary sequences determined for the intergenic regions showed the YUNR motifs to appear predominately on open hairpin loops, suggesting a regulatory role by acting as antisense RNA (Gottesman, supra, 2002). Furthermore, non-coding regulatory RNAs are between 30 and 300 nucleotide. Of the 17 upregulated intergenic regions in the present study ten fell within this definition, again indicating a regulatory RNA role. The remaining intergenic regions are much larger and have been subsequently reassigned to include variable numbers of open reading frames. These are discussed in detail below. Although non-coding regulatory RNAs of *E. coli* have been found primarily within intergenic regions (Argaman, et al., *Curr. Biol.* 11:941-950, 2001), they can also be found within genes either on the sense or antisense strand (Gottesman, supra, 2002). It is therefore possible that the larger upregulated intergenic regons may contain regulatory RNAs. Secondary RNA structures for upregulated intergenic regions of small dimensions illustrate the position of sequence homologies, open hair-pins and YUNR motifs.

(ii) Patterns of Genomic Expression Around the Most Expressed ORFs/putative IG Regions Table 2 shows the top 20 upregulated regions (incl. 2 control spots) of the *E. coli* chromosome in persister cells as detected by DNA microarray. Whilst many of these were initially identified as intergenic regions, seven of them were very large and were considered that they may act as gene regulatory regions such as the inclusion of regulatory protein binding sites (Blattner, et al., *Science* 277:1453-1462, 1997) or correspond to unmapped regions of the chromosome. More recent reference to the *E. coli* database has allowed some of these putative intergenic regions to be further characterized. Notably, IB186, IB197, IG199, IG201, and IG205 correspond to IG205 correspond to IG regions on the sense strand with ORFs being recognized on the opposing stand.

If we examine the expression level of genes adjacent to these five regions then virtually all are heavily upregulated. In this respect all five intergenic regions fall within a heavily upregulated contiguous region of the chromosome from position 287628-365529 that also includes the heavily upregulated small intergenic region, IG216 (Table 3). A number of potentially important observations were made. Notably the first of the intergenic regions (IG186) falls on the sense strand opposing not only a putative periplasmic regulator of the LysR family (yagP; 3.46) but also five upregulated ORFs relating to CP4-6 prophage. This prophage cluster encodes a toxin-antitoxin pair (ykfl—yafW) (Brown and Shaw, *J. Bacteriol.* 185:6600-6608, 2003) where in persister cells the antitoxin is slightly down-regulated (−1.06) and the toxin slightly upregulated (+1.38). Significant (100%) homology was shown between the first 30 nucleotides of IG199 (corresponding to a mid-sequence region of ykgA, an ARAC Family transcriptional regulator on the opposing strand) and either the first or last 30 nucleotides of four secondary intergenic regions variously located on the chromosome (Table 5). Also within this region of upregulated genes are further ARAC-type (ykgD, 2.36) and LysR type regulators (yahB, 3.2) and a regulator of the icIR family (yagl, 2.05).

The remaining abnormal IG (IG747) is currently thought to correspond to a region of the chromosome with ORFs on both the sense and non-sense strands. These ORFs interestingly correspond to a family of prophage genes (e14 prophage, Table 4) and include both positive and negative regulators of expression. The whole cluster of genes is in an upregulated region that includes not only IG747, but also the heavily upregulated ORFs, mcrA and stfE (Table 2) and IG754 (Table 2). This identified cluster is flanked by a regulator of the merR family (ycgE, −1.08). merR regulators are thought to activate sub-optimal sigma(70)-dependent promoters, through response to environmental stresses. Sigma 70 (rpoD, −3.14) and Sigma E (rpoE, −2.19; rseA, −2.56) are downregulated in the array.

(iii) Homologies Between Primary and Secondary Intergenic Regions/ORFs

Figure 5:
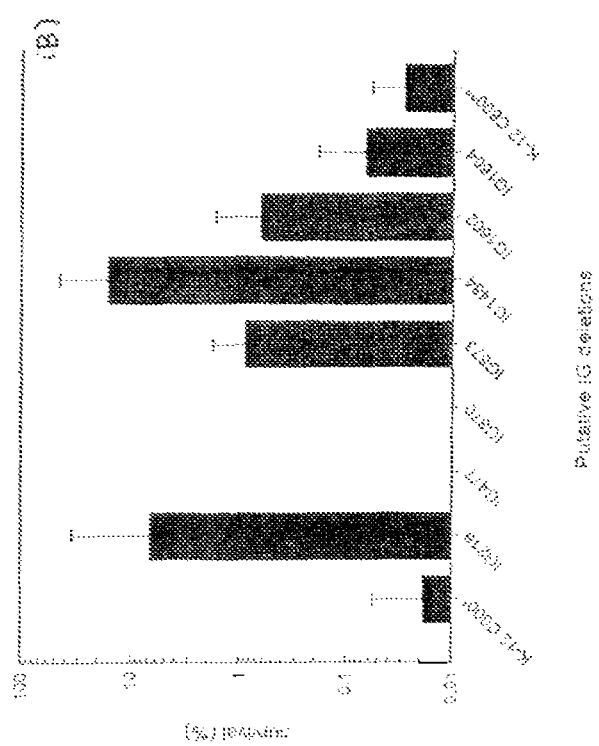
FIG. 5. Susceptibility of putative intergenic deletion clones towards cetrimide USP. Data presented are mean values generated from several putative deletion clones for each intergenic region. Deletion of intergenic regions achieved by replacement with a chloramphenicol resistance marker. (A) Putative intergenic deletion clones exposed to 0.6 μg/ml cetrimide USP for 1 hour. (B) Putative intergenic deletion clones exposed to 2.0 μg/ml cetrimide USP for 1 hour.
Figure 5:
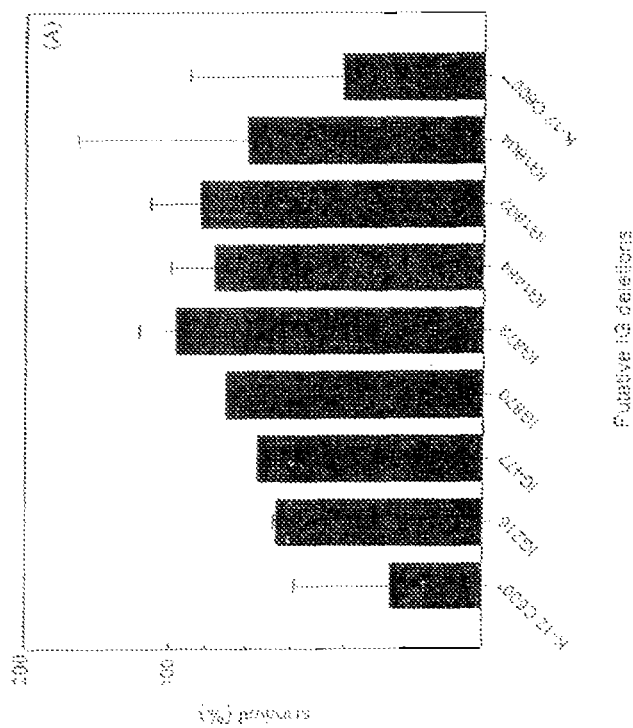

BLAST searches of the 18 putative intergenic regions of interest revealed that in six cases (IG754, IG216, IG1325, IG199, IG747 & IG477) there was significant homology (20-80 nt) not only with other heavily upregulated intergenic regions (IG870 IG873; 30nt 93% match) but also with eleven secondary intergenic regions (Table 5). Interestingly the majority of homology matches corresponded not only to the end sequence of the primary intergenic region, but also to regions on open hairpin loops with associated YUNR motifs (FIG. 5). Of particular note was that IG199, part of the upregulated genomic sequence (Table 3) contained a 30 nt sequence that had 100% homology to four different secondary intergenic regions. IG1325 possessed an 86 nt sequence that was matched (100%) by two other secondary IG regions. Genes adjacent to these secondary IG regions were generally expressed to a similar extent as in control populations. Notably however lit part of the e14 prophage system was adjacent to secondary IG IG745 and upregulated. Both IG745 and IG754 appear within the smaller upregulated genomic region (Table 4). Lit encodes for a head protein in T4 bacteriophage that is responsible for the total and universal suppression of translation. Thus, in the intact T4 phage lit halts translation of bacterial proteins in favor of viral translation and eventual lysis (Bergsland, et al., *J. Mol. Biol.* 213:477-494, 1990). In the prophage, such functions are obvious candidates for induction of quiescence/persistence.

Homologies between primary intergenic sequences and secondary gene sequences (Table 6) were detected but only for nucleotide sequences of <20. Interestingly, there were two matches of 14 and 18 nucleotides for IG873 for yagM and ykgM respectively. The homologous sequences related to a single region of IG873 of 22 nucleotides. Both ykgM and yagM code for putative proteins that were in the 50 most highly expressed regions (expression levels of 8.02 and 5.90 respectively) and yagM corresponds to the CP4-6 prophage system. A number of the up- and downstream genes relating to these homologies were within the genomic sequences highlighted in Tables 3 and 4. (i.e. ykgI, ykgD, ymfE, eaeH, yagN, yagL, icdA, ymfE)

(iv) Genomic Homologies Relating to Secondary Intergenic Regions

Blast searches were conducted using the sequence information for eleven secondary intergenic regions identified in Table 5. Homologies below 17 nt matches were ignored. In total there were 72 matches corresponding to spots on the microarray for which expression levels were known. Unpaired t-tests were performed to compare the expression levels in these homologous regions with the net expression levels of the whole array. Genomic expression was significantly upregulated in these regions (P=83%) and in the corresponding upstream (P=87%) and downstream genes (P=80%). These homologies are presented in Table 7.

Knockout Phenotypes

Knockout mutants were generated by replacement of appropriate intergenic regions with a chloramphenicol resistance element. Selection of putative replacement knockouts was on chloramphenicol agar after overnight enrichment of the electroporated cells in chloramphenicol broth. Using this method, a number of intergenic knockouts were made to *E. coli* K-12 C600::mTn5gusA-pgfp21 with respect to IG216, IG477, IG870, IG873, IG1602, IG1604 and IG1484. After multiple attempts intergenic knockouts could not be generated for the residual intergenic regions of interest, suggesting that their deletion is lethal to the cells. Confirmation of the position of insertion of the chloramphenicol gene was made by PCR between the flanking regions of the IG followed by size analysis and sequencing of the amplicon.

Intergenic knockouts were subjected to treatment with two concentrations of cetrimide USP and survival estimated by plate counts. Results are shown in FIG. 5. Susceptibility of all the developed clones was substantially reduced from that of controls. This was particularly apparent with IG216, IG873, IG1484 and IG1602 where susceptibility was profoundly changed at both the lower and higher treatment level 4.

Conditional Expression/antisense Suppression of Target Genes

A panel of ORFs and intergenic regions were selected for further study (Table 9). These had been identified as candidate genes for the control of persistence in bacterial populations (above). The approach undertaken was to generate mutants of *E. coli* that were under the control of an inducible promoter and either suppressed, through the synthesis of an appropriate antisense RNA, or over-expressed the targeted sequences.

Methods

Organisms, Plasmids and Maintenance

*Escherichia coli* C600-3004 and CC118 were obtained from Mary Berlyn at the *E. coli* Genetic stock centre and Colin Manoil and Jon Beckwith at the Harvard Medical School (Manoil, et al., *PNAS* 82, 8129-8133, 1985) respectively. *E. coli* strains were maintained on either LB or nutrient agar at 4° C. after overnight incubation at 37° C. *E. coli* strains carrying plasmids required the addition of appropriate selective agent(s) to culture media to ensure the maintenance of the respective plasmid (Table 2). Long-term storage of both strains was achieved using the Protect™ bacterial preservation system (Technical Service Consultants) or in 50% glycerol and cultures were stored at −80° C.

Growth in Liquid Culture

Liquid cultures were produced in LB (10 g/L tryptone, 5 g/L yeast extract, 10 g/L NaCl, pH 7.0) or nutrient broth (Oxoid). Approximately 4-5 colonies were used to inoculate a universal bottle containing 5 ml of media. Cultures were incubated (16-18 hours) at 37° C. in an orbital shaker at 200 rpm. A volume of 1 ml of these starter cultures were used to inoculate 50 ml of fresh media held within incubated 250 mL Erlenmeyer flasks. Cells were harvested at exponential or stationary phase, as assessed by optical density measurements at 470 nm.

Generation of Conditional Overexpression and Suppressed Strains

The generation of *E. coli* mutant strains was based upon the methods described by Choi, et al. (*Nat Methods.* 2 (6), 443-8, 2005). This method relies upon inserting a mini-transposon (mini-Tn7) into a non-essential site-specific region of the *E. coli* chromosome (attTn7 site) and is described below. Briefly, PCR amplified sequences corresponding to the target sequences were flanked by BamH1 and Xho1 restriction sites and ligated into pUC18R6KTminiTn7T-LAC at its multiple cloning site in either the sense or antisense orientation and were over-expressed or suppressed respectively. Transcription of targeted sequences was under the control of an inducible Lac promoter, enabling controlled expression or antisense suppression of the identified target genes.

Vector Construction

Vector pUC18 mini-Tn7T-LAC was obtained from Choi, et al., (supra, 2005) and was modified in the present study to contain OriT and the R6K-γ origin of replication to promote the transfer of the vector in conjugation events and allow subsequent suicide delivery into the recipient *E. coli* CC118 respectively. The modified vector, designated the pUC18R6KTminiTn7T-Lac inducible vector, was maintained in *E. coli* S17-1 λ pir and isolated from this host strain using the Qiagen maxi plasmid extraction kit, following manufacturer instructions.

Primary PCR Reactions for the Amplification of Target Sequences Flanked by BamH1 and Xho1 Restriction Sites Genomic DNA was used as template for primary PCR. The Genomic DNA isolation kit (Qiagen) was used to isolate genomic DNA from *E. coli* C600-3004 following the manufacturer's guidelines. All PCR reactions completed in the present study were performed in 0.2 ml thin-walled PCR tubes (Sigma) using a T-gradient thermal cycler (Biotetra). Primary PCR reactions were carried out using the Expand high fidelity PCR system (Roche) according to manufactures guidelines. Primers with BamH1 and Xho1 restriction sites together with the thermal cycle programmes used for amplification of the targets listed in Table 9 are detailed in Table 11. PCR products were purified using a QIAquick PCR purification kit (Qiagen) and A-tailed. A-tailing was carried out using 100-200 ng DNA, 1 µl (x10) taq buffer (Roche), 0.4 µl 0.5 mM dATP (Bioline), 1 µl taq (Roche) and mixtures were incubated for 20 min at 72° C.

pGEM T-easy Cloning and Sequence Verification

Target sequences flanked with BamH1 and Xho1 restriction sites were ligated with pGEM T-easy vector (Promega) at the multiple cloning site of the vector according to the manufacture's guidelines. Competent XL-1 Blue *E. coli* cells (Stratagene) were achieved according to the method described by Inoue, et al. (*Gene* 96, 23-28, 1990) and transformed with the target sequences and pGEM T-easy vector ligation products. Transformations were performed by subjecting competent cells to heat shock, whereby 5 µl of ligation product was gently mixed with 100 µl competent cells and was incubated on ice for 30 min. Following incubation on ice, the cells were rapidly transferred to a preheated water bath set at 42° C. for 45 s. The cell suspension was then left on ice for 2 min and incubated non-selectively for 1 h at 37° C. in 1 ml LB broth. The cell suspension was then plated into LB agar supplemented with 100 µg/ml ampicillin (Fluka) to promote selection of transformants and incubated for 16h at 37° C.

The correct nucleotide sequence of the target sequences flanked by BamH1 and Xho1 restriction sites was verified using the ABI Prism® BigDye™ terminator cycle sequencing ready reaction kits (Applied Biosystem). Sequencing was performed by Paul Fullwood and mark Bond at the Sequencing Facility within the University of Manchester using commercial T7 and SP6 promoter primers (Invitrogen). Sequences were analyzed using the Chromas (version 2.3) software package.

Cloning into pUC18R6KTminiTn7T-Lac Inducible Vector

DNA was isolated from XL-1 Blue *E. coli* cells containing pGEMteasy clones using a Qiagen maxi plasmid extraction kit, following the manufacturer's instructions and digested with BamH1 and Xho1 restriction enzymes (MBI Fermentas) to excise target sequences from the pGEM T-easy vector. Digests were carried out with approximately 1 µg pGEM T-easy vector containing target sequences, 4 µl Tango Buffer (MBI Fermentas), 21 µl BamH1, 1 µl Xho1 and nanopure water (Sigma) to 20 µl. Digests were incubated at 37° C. for 2.5 h and subjected to agarose gel electrophoresis. Bands corresponding to the target sequences were excised from the gel and purified using a Qiagen gel extraction kit following the manufacturer's guidelines.

The pUC18R6KTminiTn7T-Lac inducible vector was similarly digested with BamH1 and Xho1. Antarctic Phosphatase (NEB) (5U) was added to the digest suspension. Following incubation at 37° C. for 2.5 h, the digest was accessed by agarose gel electrophoresis and the band corresponding to the pUC18R6KTminiTn7T-Lac inducible vector was cut from the gel and purified with a Qiagen gel extraction kit according to manufacturer guidelines.

Linearized pUC18R6KTminiTn7T-Lac inducible vector (approximately 50 ng) and target sequence (approximately 25 ng) were ligated and transformed into competent *E. coli* S17-1 λ pir as described above. Transformants were selected on LB agar plates supplemented with 100 µg/ml ampicillin and 15 µg/ml gentamicin.

Mobilisation of Target Sequences into *E. coli* CC118 Recipient Strain

Target sequences integrated at the multiple cloning site of pUC18R6KTminiTn7T-Lac inducible vector were transferred into the *E. coli* CC118 host strain by conjugation. This was achieved using a tri-parental conjugation with S17-1 λpir carrying the tranposase vector pTNS2 obtained from Choi, et al. (supra, 2005), *E. coli* S17-1 λ pir carrying the pUC18R6KTminiTn7T-Lac inducible vector and the recipient strain *E. coli* CC118. Briefly, overnight LB broth cultures (5 ml) of the recipient strain *E. coli* CC118, *E. coli* S17-1 λ pir carrying the transposase vector pTNS2 and *E. coli* S17-1 λ pir carrying the pUC18R6KTminiTn7T-Lac inducible vector. Equal cell numbers (approx. 2 ml of overnight culture) from the three strains were harvested by centrifugation (10,000 x g, 5 min) and washed three times in 2 ml of fresh LB broth. Samples (1 ml) of each culture were mixed and re-centrifuged as described above. The pellet was re-suspended in the residual supernatant, and "spotted" onto LB agar. Plates were incubated in a sealed container at 30° C. for 20-22 h. Following incubation, the resultant "cell puddle" was emulsified in 1 ml saline (0.9% (w/v)). Harvested cells were centrifuged as described above and pellets were washed twice in saline (0.9% (w/v)). *E. coli* CC118 transformants harbouring the target sequence integrated into the attTn7 site of *E. coli* were counter selected for by exploiting the proline requirement of the *E. coli* S17-1 λ pir strains together with the gentamycin resistance conferred by insertion of Tn7. This was achieved by isolating colonies on a chemically defined simple salts agar (Al-Hiti, et al., *J. Bacteriol.* 49, 119-126, 19780) supplemented with 15 µg/ml gentamycin (Fluka) and amino acid suspension (Neidhardt, et al., *J. Bacteriol.* 119, 726-747, 1974) deficient in proline.

Verification of Generated Overexpression and Suppression Strains

Putative transformants were screened for ampicillin sensitivity, ensuring that the pUC18R6KTminiTn7T-Lac inducible vector and pNTS2 were lost. Candidate strains were assessed by PCR to verify insertion of Tn7 gene constructs.

Freshly isolated colonies were emulsified in nanopure water (20 µl) and boiled for 10 min to extract template DNA. Presence of mini-Tn7 was assessed using Tn7 specific primers (GTGTGGAATTGTGAGCGGA, SEQ ID NO: 1; and GAACTGGGTGTAGCGTCGT, SEQ ID NO: 2). Integration of Tn7 at the attTn7 site was verified by using primer pairs located in Tn7 and the chromosomal gene glmS downstream of the attTn7 (CAGCATAACTGGACTGATTTCAG, SEQ ID NO: 3; and CACGCTGAAGCCTACGCTGC, SEQ ID NO: 4, respectively). PCR reactions were performed as follows: 96° C. (5 min), 96° C. (45 s), 55° C. (45 s) 72° c. (1 min) for 30 cycles followed by a final extension at 72° C. for 5 min. PCR reactions contained 5 µl taq buffer (Roche), 1 µl 2.5 mM dNTPs, 2.5 µl 10 pml/µl forward and reverse primers, 37 µl nanopure water (Sigma), 1.5 µl template DNA, 0.5 µl taq (Roche).

Twelve target genes (Table 9) were initially identified for this work where each was intended for conditional overexpression and conditional knockout through production of antisense RNA. Of the twenty four intended transconjugants only ten could be processed through to completion within the current time frame. Progress achieved in generating overexpression and suppression strains for all twelve target sequences is detailed in Tables 12 and 13. Successfully generated over-expression and suppression strains are detailed in Table 14 and were used to determine the role of these sequences in persistence by challenge of midlog and stationary phase cultures with cetrimide USP. Failure to take some of the target gene sequences through to the final stage of validation of successful transconjugants was attributed to high AT-rich regions in the target sequence, notably IG216 and yagL. This could be overcome through alternate designs of primers.

Antimicrobial Susceptibility E. coli Strains Overexpressing and/or Antisense Suppressed with Respect to Target Genes Conditional overexpression and anti-sense suppression strains of E. coli (Table 14) were grown as liquid cultures in nutrient broth. Expression of target sense and antisense sequences was induced by addition of IPTG (Bioline), during early exponential phase, to a final concentration of 0.1 mM. Cells were grown until mid-late exponential (1.75 h after IPTG addition) or to stationary phase (14.5 h after ITPG addition), and harvested by centrifugation (10,000 x g, 10 min) at 4° C. The supernatants were decanted and the pellets suspended into equal volumes of PBS. The centrifugation and washing steps were repeated twice, after which the pellets were re-suspended in PBS to an optical density ($OD_{470\,nm}$) of 1.0, corresponding to approximately $1-2\times10^8$ cfu/ml mid-exponential or stationary phase cells.

Cells were exposed to 9 µg/ml cetrimide USP for 1 hr in PBS with final concentration of $5\times10^7$ cells/ml. Controls without the addition of the biocide containing the same concentration of cells and PBS were run in parallel. Following incubation samples (0.1 ml) were removed and serially diluted in lecithin (2% w/v)—tween 80 (3% w/v) broth as a specific neutralizer of quaternary ammonium biocides (Wright, et al., J. Appd. Bacteriol, 62, 309-314, 1986). Samples of appropriate dilutions were plated, in triplicate, onto nutrient agar and colonies counted after 16 h incubation at 37° C. Survival was expressed relative to untreated control suspensions that were similarly treated with IPTG. Survival was expressed relative to untreated control samples. The susceptibility of the parental strain E. coli (CC118 towards cetrimide USP was investigated in the same experiments and was used as a reference to determine the effect of overexpression and antisense suppression of target sequences.

Validation of Induction of Expression and Suppression of Target Sequences in Generated Clones Expression of target sequences was validated by analysis of transcript levels within IPTG induced bacterial cells compared against controls. RNA was isolated from post-IPTG induced bacterial cultures. These samples were taken from ongoing samples being prepared for phenotypic assessment (above). RNA was extracted using an RNeasy mini kit (Qiagen). Purified DNA-free RNA (200 ng) was reverse transcribed using RevertAid First Strand cDNA synthesis Kit according to manufacturers protocol (Fermentas). Real-time PCR was carried out using gene-specific primer sets and using the DyNAmo Capillary SYBR Green qPCR kit (Finnzymes) according to manufacturer recommendation. Amplification was performed using Roche Light Cycler 2.0 and the data analyzed using Roche Light Cycler Software version 4.0. Standard PCR products were generated using the same primers by amplification of target genes contained within pGEM-T easy as described earlier. Standard curves were generated using a dilution series of standard concentrations for each PCR product. Triplicate samples were used for each data point. Cycling conditions included a pre-incubation step of 10 min at 95° C. Followed by 40 cycles of 95° C. for 20 seconds, 50° C. for 20 seconds, and 72° C. for 20 seconds. The amplification protocol was followed by a cooling period of 40° C. for 60 seconds.

Results

Experiments were initiated to construct mutant cell lines of E. coli in which twelve (Table 9) of the previously identified target genes for persister phenotype could be separately overexpressed in response to an exogenous inducer (ITPG) or suppressed by the conditional over expression of an inserted antisense RNA to the target sequence. Of the 24 potential mutant lines only ten could be generated in the time frame of this work. The successful mutant clones are described in Table 14. Failure to generate mutant lines for the remaining 14 targets related to difficulties in primer selection, and or other technical difficulties. A pragmatic approach was adopted and the phenotype of the 10 validated strains was determined.

Validation of Induction of Expression and Suppression of Target Sequences in Generated Clones Transcription of targeted sequences was under the control of an inducible Lac promoter, enabling their selective expression or suppression in subsequent experiments. Induction of target sequences was validated by examining transcript levels by real-time PCR from exponential phase cultures. A 10-100 fold inductions were observed in all generated strains. Variability in expression level most likely reflected efficiency of primer binding for the different constructs rather than differences in expression level.

Antimicrobial Susceptibility of Exponential Phase E. coli Overexpression and Anti-sense Suppressed Strains Results are presented in Table 15. A >2-fold change in the survival of antimicrobial treated mutant cell-lines in comparison to the parental E. coli strain was considered significant. Of the ten mutant lines tested, 6 demonstrated significant changes in the level of persister cells. Overexpression of mcrA, lit, pin and ykgK resulted in significant increases in persister cell levels in exponential phase cultures (Table 15). Suppression of ykgK, through production of antisense RNA decreased the level of persister cells >5-fold (Table 15). Surprisingly, anti-sense suppression of pin increased the incidence of persistence by 18.98 fold (Table 15), quantitative PCR after suppression of pin showed an upregulation of (>2.5 fold) of lit. It appears therefore that pin is probably a negative regulator of lit expression. This renders the data set consistent with the hypothesis that lit, ykgK, mcrA, and pin regulate expression of the persister phenotype and may be modulated through antisense RNA technologies.

Antimicrobial Susceptibility of Stationary Phase E. coli Suppression Strains

Stationary phase cultures produce more persister cells than do exponential phase cultures (Spoering, et al., J. Bacteriol. 183, 6746-6751, 2001; Keren, et al., FEMS Microbiology Letters 230, 13-18, 2004). Indeed, whereas persister cells were observed in exponential cultures of Staphylococcus aureus, Pseudomonas aeruginosa and E. coli and the levels of persister cells increased as the cultures reached stationary phase, repeated re-inoculation of a culture to maintain an early exponential phase resulted in the elimination of persister cells in those populations (Keren, et al., supra, 2004) Keren, et al., (supra, 2004). Since antisense regulation of persister phenotype requires that the target population has the corresponding sense strands in operation and since this will only become significant in stationary phase then the antisense suppressed mutant lines were reassessed when grown to stationary phase. It was anticipated that under such circumstances the reduction in persister population would be more significant. Results are presented in Table 16 and indicate the predicted impact of lit, pin, ykgK and ykgM suppression in stationary phase. Suppression of lit in stationary phase cultures resulted in over a 4-fold decrease in survival/persistence, whereas persister populations were reduced to below detectable limits for pin, ykgK and ykgM.

Discussion

Keren, et al., (supra, 2004) have attributed the presence of persisters in bacterial populations to differential expression of hipAB toxin-antitoxin modules by *E. coli*. Such attributions have been made based upon changes in the frequency of observation of the persister phenotype in populations that have been upregulated for relE, or deleted with respect to hipAB expression. Such hypotheses were re-enforced by the use of DNA expression arrays utilizing cell-collections based upon their failure to type during exposure to ampicillin. Expression arrays for cells surviving ampicillin treatment was prepared from partially lysed suspensions, and had to be incubated following treatment for 180 minutes in order for the RNA released from the lysed cells to degrade. Interestingly, hipAB is restricted to only a few bacterial species and is not present even within all *E. coli* strains (Falla et al., *Antimicrob. Agents Chemo.* 42:3282-3284, 1998). It is unlikely therefore to provide a universal explanation of biofilm recalcitrance. Other toxin:antitoxin protein pairs, that are more highly conserved, might however offer reasonable explanations of persister status.

In the current series of experiments we have observed significant heterogeneity of metabolic activity within batch cultures of *E. coli* as indicated by the expression of a chromosomal GFP marker linked to a general housekeeping gene (FIG. 1). gfp expression is therefore low in those cells that are quiescent or very slowly growing. gfp expression was noted to be very heterogeneous in batch grown cultures of *E. coli*. Use of flow cytometers with fluorescence activated cell sorting enabled the separation of sub-sets of cells with low metabolic activity. These were found to regenerate the heterogeneity of normal stationary phase cultures when collected and grown (FIG. 2). This aspect of their physiology is similar to that observed for persisters, which, when collected post-treatment, and grown regenerate the parent population (Lewis, supra, 2000; Lewis, supra, 2001). When separated from overnight or stationary phase cultures by flow cytometry and cell sorting, the sub-set of cells with low metabolic activity, as indicated by low fluorescence intensity, demonstrated a significant reduction in susceptibility towards a range of antimicrobial treatments that included quaternary ammonium based biocides and a number of antibiotics. Survival time curves were biphasic, indicating an increased proportion of persister cells in stationary phase relative to mid-log phase, and according to their fluorescence intensity. This strongly suggested that the sub-set of cells with low fluorescence intensity corresponded to persisters within the population.

Recently, Stewart, et al., (*PLOS Biol.* 3:0001-0005, 2005) elegantly demonstrated that *E. coli* cells suffer a fitness cost associated with the production of a daughter cell. Thus, binary fission could no longer be considered as a bilateral process whereby two identical cells result. Rather from each dividing cell one of the progeny can be identified as the parent and the other as the daughter cell. Each dividing parent suffers a subsequent reduction in growth rate corresponding to circa 2.2%. During growth in batch culture the cumulative effect of the insults of multiple division cycles leads to a proportion of experienced parent-cells becoming quiescent. These authors dismiss the possibility that the dormant cells might constitute persisters because the predicted proportions in stationary phase cultures is greater than that reported for persisters (<0.0001%). This probability of persister occurrence, however, relates to mutations in hipA rather than to the phenotypic observations of persistence that variably report the level of persistence according to the severity of treatment, culture age and to the nature of the treatment agent as to be between 0.0001 and 1% of the population (Lewis, supra, 2001).

Sufya, et al., (supra, 2003) used extreme dilution to separate out aliquots of an *E. coli* suspension that contained single viable cells. These were transferred, in growth medium, to 96-well microtitre plates and the net growth rate of each clone assessed photometrically. Growth rates were normally distributed within the donor population and would correspond, not only to the fitness costs associated with prior parenthood predicted by Stewart, et al., (supra, 2005) but also to the levels of fluorescence intensity observed in the present study. One implication of making this association would be that the fitness costs become diluted when quiescent cells are removed from the culture or when the bulk of cells die and lyse. Also supporting the view that the persister phenotype relates to low metabolic activity is the observation, here, that persisters have less than 1% of the levels of RNA transcription than do the bulk of the population.

Notable in the present experiments, is that all of the overexpressed ORFs recorded by Keren, et al., (supra, 2004) were either downregulated or unchanged from control in our experiments. This implies that their overexpression relates to a post-stress response of the recovered persisters, given the 180 minutes exposure period prior to RNA extraction, rather than to the spontaneous generation of persisters within an actively growing culture.

With respect to the current study, a number of candidate sequences are identified that were upregulated against a background of general RNA suppression. Seventeen of the 22 most highly expressed regions, detected on microarrays, corresponded to intergenic sequences rather than to genes with known regulatory functions or gene products (Table 2). Intergenic regions are non-coding spans of DNA that appear between open reading frames and lack obvious promoters/start-stop codons for translation. In *E. coli,* the average distance between genes is 118 bp (Blattner, et al., supra, 1997) and the size of the intergenic regions upregulated in persisters isolated here ranged from 35 bp to over 10 kbp. Large intergenic regions have been suggested to have a regulatory role or may contain previously annotated ORFs (Blattner, et al., supra, 1997). Although difficult to detect because of the lack of obvious start and stop sequences, the majority of non-coding RNA found in at least *E. coli* (Argaman, et al., supra 2001) have been located within intergenic regions. Analysis of the small upregulated intergenic regions here indicated that these sequences are not simply spacers between genes, but are regulatory RNAs, a subset of noncoding RNA. In addition, a 30 nt sequence motif of the large primary IG199 is repeated in four separate locations within the *E. coli* K-12 chromosome (Table 3) and is suggestive of a non-coding RNA regulatory role of this region.

Non-coding regulatory RNAs appear to be ubiquitous, are reasonably well conserved (Gottesman, supra, 2002) and play a pivotal role in the regulation of gene expression in bacteria in response to diverse environmental changes (Argaman, et al., supra, 2001; Wassarman, et al., *Genes Dev.* 15:1637-1651, 2001; Zhang, et al., *Mol. Microbiol.* 50:111-1124, 2003). Specifically, regulatory RNAs regulate transcription by modulating the activity of proteins (Wagner, et al., *Encyclopedia of Life Sciences,* 2000), or by acting as antisense RNA by base pairing with the target RNA (Wagner, et al., supra, 2000; Zeiler, et al., "RNA Structure and Function," Cold Spring Harbour Lab. Press, Plainview, N.Y., pp. 437-464, 1998). Regulatory RNAs have been found to regulate other biological processes including protein degradation, chromosome replication and translocation (Storz, *Science* 296:1260-1263, 2002).

The functions of regulatory RNA together with the putative non-coding regulatory RNAs identified within the upregulated intergenic regions in persisters in this study, provide novel drug targets to combat bacterial persistence. Association of ncDNA and associated intergenic regions is novel and suggests that they may embody functions that are related to the adoption of persister status. As such these intergenic regions, and binding motifs within them, represent novel targets for control of persistence. This might be positive and induce persistence in conditions where biomass increases are to be controlled whilst maintaining a viable population, or it might involve abolition of the persister state within a population of bacteria prior to some antimicrobials treatment (i.e. antibiotic therapy or disinfection). As such control of persistence offers the possibility to decrease treatment concentrations for antibacterial formulations and to enhance.

IG201, IG199, IG197, IG186, IG870 and IG205 were highly expressed in the persister cells and corresponded to large intergenic regions that were several thousand nucleotides in length. All of these, with the exception of IG870, were adjacent to heavily upregulated ORFs. When mapping these intergenic regions together with their adjacent genes and ORFs, it was observed that they all fell within a contiguous region of the chromosome, from nucleotide position 287628-365529, most of which was heavily upregulated. This region includes the CP4-6 prophage ORFs associated with, amongst other things, a toxin-antitoxin protein pair (ykfl:yafW; Brown and Shaw, supra, 2003) and a number of transcriptional regulators corresponding to the ARAC (ykgA, ykgD, iclR, yagI) and LysR (yagP, yahB) families.

Martin, et al., (*Mol. Microbiol.* 37:978-979, 2000) showed that overexpression of the ARAC regulator ykgA slowed growth significantly but did not directly affect antibiotic susceptibility nor did it affect expression of marlsox and rob regulon promoters. The function of the other putative regulators in this region is unknown but the LysR family characteristically act through a co-regulatory molecule. All of these remain potential targets against the persistence phenotype. The CP4-6 prophage region is of particular interest since, it not only acts through a toxin:antitoxin coupled pair of proteins, but it has also been suggested that the translational inhibitors (toxins) encoded within this cryptic phage might be associated with the onset and spread of antibiotic resistance (Walker, et al., *J. Bacteriol.* 186:-866-869, 2004).

One other highly expressed large IG region was IG747. This intergenic region is now recognized to contain a large number of e14 prophase genes, the majority of which are upregulated in persister cells. Included here are both positive and negative regulators (downregulated) of lit, pin and mcrA. Interestingly, the cryptic prophages of the e14 class also encode for toxin-antitoxin pairs and have been associated not only with programmed cell death (Gottesman, *PNAS* 95:2731-2732, 1998) but also with limitation of the copy number of acquired plasmids. lit, pin and mcrA appear within this upregulated region and are also amongst the most highly expressed regions of the array. Interestingly the upregulated region associated with IG747 includes not only mcrA but also IG754. The RNA product of IG754 appears to be a classical regulatory RNA, appears within the top 20 upregulated regions, and is adjacent to a down-regulated transcriptional regulator of the MerR Family. MerR regulators have been shown to activate sub-optimal sigma (70)-dependent promoters. Genes encoding Sigma 70 (rpoD) and Sigma E (rpoE, rseA) are heavily downregulated in the array.

Sequence analysis of the small upregulated intergenic regions revealed that all, but IG1604, contained one or more YUNR-motifs within hairpin loops of the secondary RNA structure. This strongly suggests that they encode for non-coding, regulatory RNA. Putative insertional knockouts were constructed for six of the nine smaller intergenic regions, and IG870, all of which were associated with profound changes in persister phenotype as detected through exposure to quaternary ammonium biocides.

Sequence homology implies structural homology, and, less certainly, functional similarity (Pallen, et al., *BMN Microbiol.*, 2005). BLAST analysis of the upregulated intergenic regions against the *E. coli* K12 genome showed that six contained significant (>95%) homology (20-100 bp) with other upregulated intergenic regions, and/or secondary intergenic regions (secondary intergenic regions). In several instances secondary intergenic regions were associated with strongly up-, or downregulated genes and gene families, and some showed sequence homology to more than one primary intergenic region.

In most cases the sequence homology was between YUNR-motifs on open hairpin loops. Significant (94%) homology was shown between the upregulated IG873 (18 nt) and ykgM, also within the highly expressed genes. Both the primary intergenic regions (Table 2) together with the secondary intergenic region identified in Table 5 are likely to act as co-regulators at some other point on the genome. Homology searches between the secondary intergenic regions and the residual chromosome revealed a high detection rate for matches of >18 nt. Thus six primary intergenic regions show homology to eleven secondary intergenic regions that in turn match to over 70 regions of the chromosome. The latter are mainly comprised of small intergenic DNA and are interposed between significantly upregulated genes, many of which are found within two hot-spots of expression in persister cells (Tables 3 and 4). We propose that the primary intergenic regions identified in the present study represent the initiators of regulatory cascades that induce and maintain a state of quiescence in a population of bacteria.

We conclude that cells are maintained in a persister state through physiologies mediated by regulation of the e14 and CP4-6 prophage assemblies, possibly involving toxin:antitoxin pairs of proteins, together with a cascade of non-coding regulatory RNAs that globally regulate metabolism. Under such suppression the majority of mRNA degrades and the cells enter a quiescent state in which they become tolerant of inimical chemical stress. Such regulatory systems offer potential targets through which persistence might be moderated either to activate the cells and render them antibiotic sensitive (persisticide) or to induce quiescence as a form of population control.

The present study identifies a number of potential mechanisms by which *E. coli* regulates gene expression in persister cells and "choose" to survive. One such potential mechanism of regulation is phase variation, mediated through expression of persister genes reported here, through mcrA (Table 7). Phase variation is the process whereby bacteria undergo reversible on/off switching of gene expression, and is paralleled by the temporary expression of a persister cell state.

Located with the e14 prophage region of *E. coli*, mcrA encodes the 5-methylcytosine-specific restriction endonuclease B protein, responsible for restriction of DNA at 5-methylcytosine residues. Restriction-modification systems in a number of bacterial pathogens are subjected to phase variation. Srikhanta et al. (2005) recently demonstrated a phase variable global regulatory role for a type III restriction-modification system in *Haemphilus influenzae* and hypothesized that phase variation may be a frequently used mechanism for the multiple control of genes in other bacteria. Interestingly, Srikhanta et al. (2005) also find that the phase variable regulation of the type III restriction-modification system in *Haemphilus influenzae* influences the expression of multiple genes with common functions (heat shock proteins). This could be similar to mcrA, where the expression of this gene is involved in the global control of other persister genes.

TABLE 1

Susceptibility of various fractions of a mid-log phase nutrient broth culture of *E. coli* K-12 C600::mTn5gusA-pgfp21 separated according to fluorescence intensity (FI) by FACS Vantage cytometer and exposed to various antimicrobials for 1 hour. (bacitracin, 40 min). Data indicates the percentage survival relative to untreated controls. Standard deviation of triplicate data is given in parenthesis.

| Fluorescence Fraction | Amikacin (0.75 μg/ml) | Bacitracin (0.7 mg/ml) | Cetrimide USP (0.5 μg/ml) | Cipro-floxacin (0.05 μg/ml) | Tetra-cycline (40 μg/ml) |
|---|---|---|---|---|---|
| Control 0-100% | 39 (3.0) | 57 (8.5) | 18 (3.4) | 40 (0) | 32 (2.1) |
| 95-100%/FI | 32 (0) | 34 (4.6) | 2.5 (0.97) | 35 (3.6) | 16 (1.0) |
| 0-5%/FI | 68 (17) | 83 (1.5) | 22 (3.7) | 44 (2.0) | 39 (2.5) |

TABLE 2

Most highly upregulated ORFs and intergenic regions in persister cell populations together with levels of expression in upstream and downstream regions. Expression levels (exp) are expressed as antilogs.

| ORF/IG | Expression Level(ExpL) | Size (bp) | Upstream ORF | (Exp) | Downstream ORF | (Exp) |
|---|---|---|---|---|---|---|
| IG1484 | 18.77 | 102 | yfbL: putative aminopeptidase | (−1.18) | yfbM: hypothetical protein | (−1.26) |
| IG201 | 18.26 | 1655 | b0302: hypothetical protein | (3.13) | ykgD: putative ARAC-type regulatory protein | (2.36) |
| IG754 | 16.14 | 106 | pin: e14 prophage; inversion of adjacent DNA | (3.62) | mcrA: e14 prophage; enzyme involved in the degradation of DNA: restriction of DNA at 5-methylcytosine residues | (13.54) |
| IG2037 | 16.00 | 60 | yhaB: hypothetical protein | (1.05) | b3122: hypothetical protein | (−1.21) |
| IG216 | 14.70 | 242 | yahK: putative dehydrogenase, NAD (P)-binding | (1.40) | yahL: hypothetical protein | (8.33) |
| IG1604 | 14.18 | 117 | yffN: CPZ-55 prophage | (−1.06) | yffO: CPZ-55 prophage | (1.78) |
| IG1325 | 14.17 | 117 | yeeO: Hypothetical protein | (−1.06) | cbl: transcriptional regulator cys regulon: accessory regulatory circuit affecting cysM | (1.09) |
| IG199 | 14.09 | 1848 | tra5_5: putative IS transposase | (not present on array) | b0302: hypothetical protein | (3.13) |
| mcrA | 13.54 | 834 | pin: e14prophage; inversion of adjacent DNA | (3.62) | ycgW: hypothetical protein | (2.69) |
| IG870 | 13.30 | 2095 | ycjG: L-Ala-D/L-Glu epimerase, a muconate lactonizing enzyme | (1.68) | ycjZ: transcriptional regulator (LysR family) | (1.29) |
| IG1602 | 11.38 | 190 | intZ: CPZ-55 prophage; putative integrase | (−1.54) | yffL: CPZ-55 prophage | (1.20) |
| IG873 | 11.38 | 315 | ycjZ: putative transcriptional regulator (LysR family) | (1.29) | mppA: periplasmic murein tripeptide (L-Ala-gamma-D-Glut-m-DAP) permease | (1.44) |
| IG197 | 10.38 | 2017 | ykgL: hypothetical protein | (6.83) | eaeH: attaching and effacing protein, pathogenesis factor | (2.45) |
| IG747 | 9.79 | 1863 | lit: e14 prophage; like phage T4 late gene expression | (4.10) | ycfK: e14 prophage | (1.71) |
| IG186 | 9.56 | 10,759 | yagJ: CP4-6 prophage | (3.73) | yagU: hypothetical protein | (6.97) |
| ykgK | 9.43 | 591 | yagZ: hypothetical protein | (2.81) | ykgL: hypothetical protein | (6.83) |
| IG205 | 9.35 | 5009 | ykgG: putative transporter | (2.00) | betT: high-affinity choline transport | (1.43) |
| IG477 | 8.58 | 35 | ybgL: putative lactam utilization protein | (1.08) | nei: endonuclease VIII | (1.21) |
| yahL | 8.33 | 816 | yahK: putative dehydrogenase, NAD (P)-binding | (1.40) | yahM: hypothetical protein | (4.27) |
| stfE | 8.30 | 540 | tfaE: e14 prophage; putative tail fibre assembly | (2.86) | pin: e14 prophage: inversion of adjacent DNA | (3.62) |
| ykgM | 8.02 | 264 | ykgL: hypothetical protein | (6.83) | eaeH: attaching and effacing protein, pathogenesis factor | (2.45) |
| IG1803 | 7.71 | 69 | ygcU: putative oxidoreductase subunit | (1.39) | ygcW: putative deoxygluconate dehydrogenase | (1.01) |

TABLE 3

Upregulated hotspot regions in persister cells related to intergenic regions, IG186, IG197, IG199, IG20, IG205 and IG216

| Gene | Description | Level of Expression (antilog) |
|---|---|---|
| yagH | CP4-6 prophage; putative xylosidase/ arabinosidase | −1.14 |
| yagI | CP4-6 prophage; putative transcriptional regulator (IcIR family) | 2.05 |
| argF | CP4-6 prophage; ornithine carbamoyltransferase 2, catalytic chain F | 1.33 |
| insB_3 | CP4-6 prophage; IS1 protein InsB | not present on array (IG182 = −1.18) |
| insA_3 | CP4-6 prophage; IS1 protein InsA | not present on array (IG182 = −1.18) |
| yagJ | CP4-6 prophage | 3.73 |
| yagK− (IG186)+ | CP4-6 prophage | 4.63 |
| yagL− (IG186)+ | CP4-6 prophage; DNA-binding protein | 7.10 |
| yagM− (IG186)+ | CP4-6 prophage | 5.90 |
| yagN− (IG186)+ | CP4-6 prophage | 5.30 |
| intF− (IG186)+ | CP4-6 prophage; putative phage integrase | 4.12 |
| yagP− (IG186)+ | putative periplasmic regulator | 3.46 |
| yagQ− (IG186)+ | hypothetical protein | 2.21 |
| yagR− (IG186)+ | putative cofactor-binding oxidoreductase. yagR-yagS-yagT may be a heterotrimeric xanthine dehydrogenase | 2.50 |
| yagS− (IG186)+ | putative oxidoreductase. NADH-binding domain yagR-yagS-yagT may be a heterotrimeric xanthine dehydrogenase | 2.81 |
| yagT− (IG186)+ | putative oxidoreductase, Fe-S subunit. yagR-yagS-yagT may be a heterotrimeric xanthine dehydrogenase | 2.03 |
| yagU | hypothetical protein | 6.97 |
| ykgJ | putative ferredoxin | 2.87 |
| yagV | hypothetical protein | 4.08 |
| yagW | hypothetical protein | 2.15 |
| yagX | hypothetical protein | 2.26 |
| yagY | hypothetical protein | 3.87 |
| yagZ | hypothetical protein | 2.81 |
| ykgK | putative regulator | 9.43 |
| ykgL | hypothetical protein | 6.83 |
| ykgM− | putative ribosomal protein | 8.02 |
| IG197+ | | 10.38 |
| eaeH | attaching and effacing protein, pathogenesis factor | 2.45 (IG198 = −1.05) |
| b0298 | putative transposase-related protein | not present on array (IG198 = −1.05) |
| tra5_5 | putative IS tranposase | not present on array (IG198= −1.05) |
| ykgA− IG199+ | putative ARAC-type regulatory protein | 3.79 14.09 |
| ykgB− IG199+ | putative membrane protein | 2.71 14.09 |
| b0302 | hypothetical protein | 3.13 |
| ykgI− IG201+ | hypothetical protein | 6.66 18.26 |
| ykgC− IG201+ | putative oxidoreductase | 3.39 18.26 |
| ykgD | putative ARAC-type regulatory protein | 2.36 |
| ykgE | putative dehydrogenase subunit | 1.78 |
| ykgF | hypothetical protein | 3.93 |
| ykgG | putative transporter | 2.00 |
| b0309− IG205+ | hypothetical protein | 6.17 9.35 |
| ykgH− IG205+ | hypothetical protein | 4.53 9.35 |
| betA− IG205+ | choline dehydrogenase, a flavoprotein | 1.42 9.35 |
| betB− | NAD+−dependent betaine aldehyde dehydrogenase | 2.40 |
| IG205+ | | 9.35 |
| betI− | probably transcriptional repressor of bet genes | 3.02 |
| IG205 | | 9.35 |
| betT | high-affinity choline transport | 1.47 |
| yahA | hypothetical protein | 3.04 |
| yahB | putative transcriptional regulator (LysR family) | 3.20 |
| yahC | putative membrane protein | 2.67 |
| yahD | putative transcriptional factor | 3.22 |
| yahE | hypothetical protein | 2.01 |
| yahF | putative acyl-CoA synthetase | 1.90 |
| yahG | hypothetical protein | 2.14 |
| yahH | hypothetical protein | 1.13 |
| yahI | putative carbamate kinase | 4.25 |
| yahJ | putative deaminase | 2.83 |
| yahK | putative dehydrogenase, NAD(P)-binding | 1.40 |
| IG216 | Intergenic region | 14.7 |
| yahL | hypothetical protein | 8.33 |
| yahM | hypothetical protein | 4.27 |
| yahN | putative cytochrome subunit of dehydrogenase. | 2.79 |
| yahO | hypothetical protein | 5.50 |
| prpR | regulator for prp operon. (EBP family) | 2.09 |
| prpB | putative carboxyphosphonoenolpyruvate mutase | 1.43 |
| f148 | hypothetical protein | 4.45 |
| prpC | methylcitrate synthase (citrate synthase 2) | 1.92 |
| prpD | 2-methyl citrate dehydratase | 3.25 |
| prpE | putative acetyl-CoA synthetase of the propionate catabolism operon | 2.51 |
| codB | cytosine permease/transport. (NCS1 family) | 3.70 |
| codA | cytosine deaminase | 2.60 |
| cynR | cyn operon positive regulator. (LysR family) | 2.12 |
| cynT | carbonic anhydrase | 1.65 |
| cynS | cyanate aminohydrolase (cyanase) | 4.74 |
| cynX | cyanate transport. (MFS family) | 2.23 |
| lacA | thiogalactoside acetyltransferase | 6.05 |
| lacY | galactoside permease (lactose permease, M protein) (MES family) | 1.55 |
| lacZ | beta-D-galactosidase | −1.33 |

Genes listed in 'ascending order' as found on the E. coil K. 12 chromosome (yagI starts at position 287628, lacZ ends at position 365529). Grey highlighted regions indicate overlap with large Intergenic regions.

TABLE 4

Upregulated hotspot regions in persister cells related to intergenic regions IG747 & IG754, mcrA and stfE

| Gene | Description | Level of Expression (antilog) |
|---|---|---|
| ymfC | pseudouridine synthase | 1.28 |
| icdA | e14 prophage; isocitrate dehydrogenase, specific for NADP+ | −1.29 |
| ymfD | e14 prophage; putative SAM-dependent methyltransferase | 2.83 |
| ymfE | e14 prophage | 7.11 |
| lit | e14 prophage; like phage T4 late gene expression | 4.10 |
| intE− | e14 prophage; integrase. | 5.93 |
| ymfG− | e14 prophage; putative exisionase | 2.32 |
| ymfH− | e14 prophage | 2.35 |

TABLE 4-continued

Upregulated hotspot regions in persister cells related to intergenic regions IG747 & IG754, mcrA and stfE

| Gene | Description | Level of Expression (antilog) |
|---|---|---|
| ymfI+ | e14 prophage | 2.58 |
| ymfJ− | e14 prophage | 1.54 |
| ymfK− | e14 prophage; putative phage repressor | −1.03 |
| b1146+ | e14 prophage; putative regulator | 2.85 |
| ymfL+ | e14 prophage; putative negative regulator | −1.18 |
| ymfM+ | e14 prophage | 2.69 |
| ymfN+ | e14 prophage; putative terminase | 1.83 |
| ymfR+ | e14 prophage | 1.82 |
| ymfO+ | e14 prophage | 1.78 |
| ymfP+ | e14 prophage | 1.70 |
| ymfQ+ | e14 prophage | 3.41 |
| ycfK | e14 prophage | 1.71 |
| ymfS | e14 prophage | 6.50 |
| tfaE | e14 prophage; putative tail fiber assembly | 2.86 |
| stfE | e14 prophage; putative tail fiber protein | 8.30 |
| pin | e14 prophage; inversion of adjacent DNA | 3.62 |
| IG754 | Intergenic region (primary upregulated IG) | 16.14 |
| mcrA | e14 prophage; restriction of DNA at 5-methylcytosine residues. 5-methyl-cytosine-specific restriction endonuclease B. | 13.54 |
| ycgW | hypothetical protein. | 2.69 |
| ycgX | hypothetical protein | 1.62 |
| ycgE | putative transcriptional regulator | −1.08 |

Genes listed in 'ascending' order as found on the *E. coli* K-12 chromosome (ymfD starts at position 1196090, ycgW ends at position 1211226). Grey highlighted regions indicate overlap on + & − strand with IG747.

TABLE 5

Homology between primary intergenic regions and other intergenic regions

| Primary IG | Secondary IG | Size (bp) | Homology to Primary IG number (% similarity) | Expression Level (exp) (antilog) | UP | exp | Down | exp |
|---|---|---|---|---|---|---|---|---|
| IG754 | IG745 | 2321 | 18 nt (94%) | 5.20 | icdA | −1.29 | lit | 4.10 |
| IG216 | IG1288 | 1422 | 21 nt (95%) | 1.07 | yedK | −1.20 | intG | −1.21 |
| IG1325 | IG1316 | 8720 | 86 nt (100%)* | 1.52 | yodB | −1.32 | shiA | −1.25 |
|  | IG1328 | 457 | 86 nt (100%)* | 1.14 | nac | 1.34 | erfK | 1.22 |
| IG199 | IG1377 | 7420 | 30 nt (100%)* | −1.02 | b2088 | * | yegT | 1.32 |
|  | IG681 | 1985 | 30 nt (100%)* | 1.12 | ycdS | 1.45 | tra5_3 | −1.14 |
|  | IG368 | 105 | 30 nt (100%)* | 1.12 | tra5_2 | * | renD | −1.06 |
|  | IG246 | 1303 | 30 nt (100%)* | 2.48 | yaiT | −1.04 | yaiU | 1.40 |
| IG870 | IG873 | 315 | 30 nt (93%) | 11.38 | ycjZ | 1.68 | mppA | 1.44 |
| IG873 | IG870 | 2095 | 30 nt (93%) | 13.30 | ycjG | 1.68 | ycjZ | 1.29 |
| IG747 | IG1040 | 174 | 28 nt (96%) | 1.09 | dicF | 1.06 | dicB | −1.00 |
|  | IG886 | 7663 | 33 nt (90%) | 1.08 | dbpA | 1.13 | sieB | −1.78 |
| IG477 | IG1218 | 73 | 18 nt (94%) | 1.28 | yebO | 1.16 | yobG | 1.51 |
| IG201 | No homology |  |  |  |  |  |  |  |
| IG1604 | No homology |  |  |  |  |  |  |  |
| IG1602 | No homology |  |  |  |  |  |  |  |
| IG197 | No homology |  |  |  |  |  |  |  |
| IG1803 | No homology |  |  |  |  |  |  |  |
| IG1484 | No homology |  |  |  |  |  |  |  | lit—e14 prophage; like phage T4 late gene expression #, homologies sequential*, homologous regions identical within group

TABLE 6

Genes/ORFs with sequence homology to primary intergenic regions

| Primary IG | Secondary gene/ORF | Size (bp) | Homology to Primary IG (%) | Description | Expression Level (exp) (antilog) | UP | exp | Down | exp |
|---|---|---|---|---|---|---|---|---|---|
| IG1484 | ycaM | 1623 | 15 (100%) | putative amino-acid transport protein (APC family) | 1.68 | ycaD | −1.19 | ycaN | −1.21 |
|  | yeaY | 589 | 13 (100%) | putative membrane protein | −2.25 | fadD | −1.56 | yeaZ | n.p. |
| IG754 | yihF | 1473 | 19 (94%) | hypothetical protein | −1.10 | dsbA | −1.35 | yihG | −1.42 |
|  | envR | 663 | 15 (100%) | putative transcriptional regulator | −1.12 | yhdU | n.p. | acrE | −1.04 |
| IG2037 | ycdS | 2424 | 19 (94%) | putative outer membrane protein | 1.45 | ycdR | 1.22 | ycdT | 1.15 |
|  |  |  |  |  |  |  |  | tra5_3 | −1.34 |
|  | ymfD | 666 | 14 (100%) | e14 prophage; putative methyltransferase | 2.83 | icdA | −1.29 | ymfE | 7.10 |
| IG216 | yjbM | 708 | 22 (94%) | hypothetical protein | −1.57 | yjbL | −1.13 | yibN | n.p. |
| IG1604 | yhbS | 504 | 16 (100%) | hypothetical protein | 1.07 | yhbQ | −1.08 | yhbT | −1.34 |
|  | ykgC | 1353 | 13 (100%) | putative oxidoreductase | 3.39 | ykgl | 6.67 | ykgD | 2.36 |
| IG1325 | asnW | 76 | 86 (100%) | asparagine tRNA | −1.23 | yeeN | −1.14 | yeeO | −1.06 |
| IG870 | yegO | 3077 | 17 (100%) | hypothetical protein | 1.07 | yegN | 1.15 | yegB | −1.14 |
| IG873 | yqiG | 2466 | 20 (95%) | putative membrane protein | −1.44 | yi22_5 | n.p. | yqiH | −1.34 |
|  | yagM | 855 | 14 (100%) | CP4-6 prophage | 5.90 | yagL | 7.10 | yagN | 5.30 |
|  | ykgM | 264 | 18 (94%) | putative ribosomal protein | 8.02 | ykgL | 6.66 | eaeH | 2.45 |
|  | yedV | 1359 | 14 (100%) | putative 2-component sensor protein | −2.00 | yedU | −1.09 | yedW | −1.14 |
| IG477 | first 13 nt in last nucleotides of IG1288, rest in yobG | 1422 (IG1288) 144 (yobG) | 18 (94%) | hypothetical protein | 1.51 | yebO | 1.16 | yobG | 1.51 |
|  | yeaS | 639 | 14 (100%) | hypothetical protein | −1.39 | yeaR | −1.04 | yeaT | −1.71 |
| IG1803 | idnD | 1032 | 17 (100%) | L-iodonate-5-dehydrogenase, NAD-binding | −1.27 | idnO | −1.02 | idnK | −1.06 | n.p. not present on array

TABLE 7

Blast searches for homologous regions (>17 nt) relating to secondary intergenic regions identified in Table 5

| Primary IG region | Secondary Intergenic Region (region of IG involved in similarity) | Tertiary intergenic Region/Gene/ORF | Description | Size (bp) | Homology to Secondary IG number (% similarity) | Expression Level (antilog) | Gene/ORF upstream | Expression Level (antilog) | Gene/ORF downstream | Expression Level (antilog) |
|---|---|---|---|---|---|---|---|---|---|---|
| IG1484 | IG48 (373-390) | eamA | amino acid metabolite efflux pump | 801 | 18 (100%) | 1.27 | marB | 1.14 | ydeE | 1.05 |
| | IG48 (1516-1532) | yhhT | hypothetical protein | 1131 | 17 (100%) | 1.10 | yhhS | 1.36 | acpT | not present on array |
| | IG48 (570-588) | hlyE | hemolysin E | 918 | 19 (94%) | -2.0 | ycgN | 1.10 | umuD | -1.09 |
| | IG48 (1233-1251) | emrR | regulator of plasmid mcrB operon (microcin B17 synthesis) | 531 | 19 (94%) | -1.21 | ygaH | 1.31 | emrA | -1.11 |
| | IG886 (7466-7531) | Last 6 nt in dicF, then first 60 nt of IG1040 | dicF: antisense RNA; inhibits ftsZ | dicF: 53 | 66 (93%) | dicF: 1.06 IG1040: 1.07 | ydfC | 1.03 | dicB | -1.00 |
| | IG886 (46-83) | IG1608 | intergenic region | IG1040: 174 216 | 38 (94%) | -2.0 | eutH | 1.04 | eutG | 1.16 |
| | IG886 (46-83) | IG1626 | intergenic region | 2193 | 38 (94%) | -1.48 | perM | 1.12 | hda | 1.05 |
| | IG886 (46-83) | IG2559 | intergenic region | 213 | 37 (94%) | -1.13 | frwD | 1.09 | yijP | -1.10 |
| | IG886 (46-83) | IG1040 | intergenic region | 174 | 48 (89%) | 1.07 | dicF | 1.06 | dicB | -1.00 |
| | IG886 (49-83) | IG36 | intergenic region | 7061 | 35 (95%) | -1.52 | folA | 1.00 | djlA | not present on array |
| | IG886 (48-83) | IG1612 | intergenic region | 4091 | 39 (94%) | 1.05 | tktB | -1.09 | narQ | 1.70 |
| | IG886 (48-81) | IG264 | intergenic region | 1055 | 34 (94%) | -1.29 | ykiA | 1.22 | yajF | -1.03 |
| | IG886 (48-83) | IG2000 | intergenic region | 1980 | 38 (92%) | 1.27 | yqiH | 1.47 | ygjG | -1.01 |
| | IG886 (47-83) | IG44 | intergenic region | 2180 | 37 (91%) | -1.13 | araB | -1.09 | yabJ | -1.06 |
| | IG886 (47-83) | IG1421 | intergenic region | 2566 | 37 (91%) | -1.56 | yeiI | -1.19 | yeiL | -1.19 |
| | IG886 (48-83) | b0100 | hypothetical protein | 135 | 36 (91%) | -1.55 | mutT | -1.14 | yacG | 1.01 |
| | IG886 (48-83) | o80 b0395 | hypothetical protein | 221 | 36 (91%) | -1.02 | yaiF | -1.03 | araJ | 1.25 |
| | IG886 (48-83) | IG1459 | intergenic region | 996 | 36 (91%) | 1.04 | yafA | -1.21 | yfaL | -1.09 |

TABLE 7-continued

Blast searches for homologous regions (>17 nt) relating to secondary intergenic regions identified in Table 5

| Primary IG region | Secondary Intergenic Region (region of IG involved in similarity) | Tertiary intergenic Region/Gene/ORF | Description | Size (bp) | Homology to Secondary IG number (% similarity) | Expression Level (antilog) | Gene/ORF upstream | Expression Level (antilog) | Gene/ORF downstream | Expression Level (antilog) |
|---|---|---|---|---|---|---|---|---|---|---|
| | IG886 (48-83) | IG1608 | intergenic region | 216 | 36 (91%) | −2.00 | eutH | 1.04 | eutG | 1.16 |
| | IG886 (47-83) | ygiL | putative NADPH dehydrogenase | 2019 | 36 (91%) | −1.15 | ygjK | −1.17 | ygjM | −1.50 |
| | IG886 (48-83) | IG2051 | intergenic region | 1947 | 36 (91%) | −1.83 | yraO | −1.15 | yhbO | −1.28 |
| | IG886 (48-83) | IG2201 | intergenic region | 5209 | 36 (91%) | −1.27 | yhgI | −1.43 | malT | −1.07 |
| | IG886 (48-83) | IG2492 | intergenic region | 1432 | 36 (91%) | 1.12 | hemG | −1.27 | yihD | −1.60 |
| | IG886 (48-83) | IG2649 | intergenic region | 9064 | 36 (91%) | −1.03 | nrfC | 1.14 | yjcO | 1.03 |
| | IG886 (48-83) | IG1912 | intergenic region | 3515 | 38 (92%) | −1.40 | yggG | −1.64 | yqgC | 1.07 |
| | IG886 (48-83) | intQ (1208-1277) | Qin prophage; putative transposase | 1197 | 70 (82%) | −1.61 | b1578 | not present on array | rspB | −1.15 |
| | IG1859 (118-135) | IG904 | intergenic region | 927 | 18 (94%) | 1.01 | ynaE | −1.01 | ynaF | −1.40 |
| | IG1288 (1337-1354) | IG668 | intergenic region | 3088 | 18 (100%) | −1.34 | cbpA | −1.21 | yccJ | −1.10 |
| | IG1288 (1337-1354) | IG2513 | intergenic region | 825 | 18 (100%) | 2.00 | dtd | −2.31 | yiiE | −1.19 |
| | IG1288 (1337-1354) | napD | hypothetical protein | 264 | 17 (100%) | 1.66 | napA | 1.91 | napF | 1.40 |
| | IG1288 (235-251) | feoA | ferrous iron transport protein A | 228 | 17 (100%) | −1.08 | yhgF | 1.22 | feoB | 1.10 |
| | IG1288 (1339-1355) | IG2735 | intergenic region | 656 | 17 (100%) | −1.12 | rpII | 1.64 | ytfA | −1.95 |
| | IG1288 (41-64) | pin (first 22 nt) IG754 (last 2 nt) | e14 prophage; inversion of adjacent DNA | 555 | 24 (100%) | 3.62 | stfE | 8.30 | mcrA | 13.54 |
| IG216 | IG1288 (474-493) | tdcR | threonine dehydratase operon activator protein | 345 | 20 (95%) | −1.21 | tdcA | −1.03 | yheB | 1.05 |
| | IG1288 (1337-1355) | yhaB | hypothetical protein | 561 | 20 (95%) | 1.05 | tdcR | −1.21 | yhaC | −1.10 |
| | IG1288 (1337-1355) | yneJ (first 4 nt) IG1005 (last 15 nt) | yneJ: putative transcriptional regulator (LysR family) IG1005: intergenic region | yneJ: 882 IG1005: 77 | 19 (94%) | −1.37 | yneI | −1.02 | yneK | not present on array |

TABLE 7-continued

Blast searches for homologous regions (>17 nt) relating to secondary intergenic regions identified in Table 5

| Primary IG region | Secondary Intergenic Region (region of IG involved in similarity) | Tertiary intergenic Region/Gene/ORF | Description | Size (bp) | Homology to Secondary IG number (% similarity) | Expression Level (antilog) | Gene/ORF upstream | Expression Level (antilog) | Gene/ORF downstream | Expression Level (antilog) |
|---|---|---|---|---|---|---|---|---|---|---|
| | IG1288 (1337-1355) | IG1151 | intergenic region | 276 | 19 (94%) | −1.68 | ydjO | −1.25 | cedA | 1.01 |
| | IG1288 (1337-1355) | IG1532 | intergenic region | 365 | 19 (94%) | 1.47 | fadL | −1.06 | yfdF | not present on array |
| | IG1288 (1373-1395) | xylF | D-xylose transport protein (ABC superfamily, peri bind) | 993 | 23 (91%) | −1.06 | xylA | −1.09 | xylG | 1.21 |
| | IG1288 (1337-1355) | IG2362 | intergenic region | 3188 | 19 (94%) | −1.27 | ylcI | −1.34 | nlpA | −1.61 |
| IG1325 | IG1316 (2287-2388) | eaeH | attaching and effacing protein, pathogenesis factor | 888 | 102 (83%) | 2.45 | ykgM | 8.02 | b0298 | not present on array |
| | IG1316 (972-998) | IG1324 (IG1324 WITHIN IG1323) | intergenic region | 100 | 26 (92%) | −3.93 | asnW | −1.27 | yeeO | −1.06 |
| | IG1316 (972-1075) | IG1323 | intergenic region | 2276 | 104 (98%) | −1.02 | yeeN | −1.14 | cbl | 1.09 |
| | IG1316 (972-1082) | IG1328 | intergenic region | 457 | 111 (98%) | 1.14 | nac | 1.34 | erfK | 1.22 |
| | IG1328 (305-408) | IG1323 | intergenic region | 2276 | 104 (97%) | −1.02 | yeeN | −1.14 | cbl | 1.09 |
| | IG1328 (68-94) | yitO | hypothetical protein | 429 | 27 (88%) | 2.87 | yjfN | −1.21 | yjfP | −1.15 |
| IG199 | IG200 (503-522) | pgm | phosphoglucomutase | 1641 | 20 (95%) | 1.22 | seqA | −1.73 | ybfP | −1.06 |
| | IG200 (315-333) | htrE | probable outer membrane porin protein involved in fimbrial assembly | 2597 | 19 (94%) | 1.47 | yadM | 1.12 | ecpD | −1.06 |
| | IG246 (1-493) | tra5_2 | DLP12 prophage; putative transposase for insertion sequence IS3 | 867 | 867 (100%) | not present on array | b0540 | not present on array | renD | −1.06 |
| | IG246 (1-493) | tra5_3 | b1026 putative transposase for IS3 | 863 | 863 (100%) | −1.34 | ycdT | 1.15 | b1027 | not present on array |
| | IG246 (28-894) | Tra5_4 | transposase insF for insertion sequence IS3 | 867 | 867 (100%) | not present on array | b2088 | not present on array | galD | 1.06 |
| | IG246 (91-148) | First 49 nt in back end of Ig1719, rest in front end of yfjM | IG1719: intergenic region | IG1719: 359 yfjM: 265 | 58 (87%) | IG1719: 10.2 yfjM: 1.17 | yfjL | −1.63 | yfjN | −2.24 |
| | | | yfjM: CP4-57 prophage | | | | | | | |

TABLE 7-continued

Blast searches for homologous regions (>17 nt) relating to secondary intergenic regions identified in Table 5

| Primary IG region | Secondary Intergenic Region (region of IG involved in similarity) | Tertiary intergenic Region/Gene/ORF | Description | Size (bp) | Homology to Secondary IG number (% similarity) | Expression Level (antilog) | Gene/ORF upstream | Expression Level (antilog) | Gene/ORF downstream | Expression Level (antilog) |
|---|---|---|---|---|---|---|---|---|---|---|
| | IG246 (447-465) | ycbC | hypothetical protein | 780 | 19 (94%) | −1.37 | ycbJ | not present on array | smtA | −1.16 |
| | IG368 (1-31) | IG368 | intergenic region | 1288 | 31 (100%) | −1.03 | ycdT | 1.15 | ymdE | 1.25 |
| | IG368 (1-30) | ykgA (IG199) | putative AIAC-type regulatory protein | 720 | 30 (100%) | 3.79 | tra5_5 | not present on array | ykgB | 2.71 |
| | IG681 (1955-1985) | first 3 nt in yaiT, rest in IG246 | IG246: intergenic region yaiT: hypothetical protein | IG246: 1303 yaiT: 1461 | 31 (100%) | IG246: 2.48 yaiT: −1.04 | b0370 | 1.24 | yaiU | 1.40 |
| | IG681 (1955-1985) | IG368 | intergenic region | 105 | 31 (100%) | 1.12 | tra5_2 | not present on array | renD | −1.06 |
| | IG681 (1956-1985) | ykgA (IG199) | putative ARAC-type regulatory protein | 720 | 30 (100%) | 3.79 | tra5_5 | not present on array | ykgB | 2.71 |
| | IG681 (1956-1985) | gatR | split galactitol utilization operon repressor, fragment 2 | 339 | 30 (100%) | 1.17 | tra5_4 | not present on array | gatD | 1.06 |
| | IG681 (675-695) | yhfC | putative transport | 1182 | 21 (100%) | −1.39 | ppiA | −1.12 | nirB | −1.59 |
| | IG1377 (1-32) | ykgA | putative ARAC-type regulatory protein | 720 | 32 (100%) | 3.97 | tra5_5 | not present on array | ykgB | 2.71 |
| | IG1377 (6010-6047) | IG225 | intergenic region | 329 | 38 (94%) | 2.08 | prpE | 2.51 | codB | 3.70 |
| | IG1377 (6055-6080) | IG1740 | intergenic region | 237 | 26 (96%) | −2.07 | gabT | 1.07 | gabP | −1.02 |
| | IG1377 (6010-6047) | IG222 | intergenic region | 439 | 38 (89%) | 2.27 | prpB | 1.43 | prpC | 1.93 |
| | IG1377 (6051-6086) | IG1608 | intergenic region | 216 | 32 (93%) | −2.00 | eutH | 1.04 | eutG | 1.16 |
| IG870 | IG873 (250-279) | IG870 | intergenic region | 2095 | 30 (93%) | 13.30 | ycjG | 1.68 | ycjZ | 1.29 |
| | IG873 (286-305) | yqjG | putative membrane protein | 2450 | 20 (95%) | −1.44 | yi22_5 | not present on array | ygiH | 1.11 |
| | IG873 (57-84) | ykgM | putative ribosomal protein | 264 | 18 (94%) | 8.02 | ykgL | 6.83 | eaeH | 2.45 |
| IG873 | IG870 (799-828) | IG873 | intergenic region | 315 | 30 (93%) | 11.38 | ycjZ | 1.29 | mppA | 1.44 |
| | IG871 (199-215) | yegO | hypothetical protein | 1025 | 17 (93%) | 1.07 | yegN | 1.15 | yegB | −1.14 |
| IG747 | IG886 IG1040 | see entry for primary IG882 (which is intergenic region IG1484 | intergenic region | IG882: | 60 (93%) | IG882: 1.95 | kil | 1.04 | ydaG | 1.78 |

TABLE 7-continued

Blast searches for homologous regions (>17 nt) relating to secondary intergenic regions identified in Table 5

| Primary IG region | Secondary Intergenic Region (region of IG involved in similarity) | Tertiary intergenic Region/Gene/ORF | Size (bp) | Homology to Secondary IG number (% similarity) | Description | Expression Level (antilog) | Gene/ORF upstream | Expression Level (antilog) | Gene/ORF downstream | Expression Level (antilog) |
|---|---|---|---|---|---|---|---|---|---|---|
| | (1-60) | located within IG886 | 1080 | | | | | | | |
| | IG1040 (101-148) | IG886 | 7663 | 48 (89%) | intergenic region | 1.08 | dbpA | 1.13 | sieB | −1.78 |
| | IG1040 (22-49) | ymfH | 312 | 28 (96%) | e14 prophage | 2.35 | ymfG | 2.32 | ymfI | 2.58 |
| | IG1040 (95-111) | otsA | 1425 | 17 (100%) | trehalose-6-phosphate synthase | −1.38 | yecG | −1.37 | otsB | −1.17 |
| | IG1040 (141-157) | IG1605 | 459 | 17 (100%) | intergenic region | 1.76 | yfiP | 1.04 | yffQ | 2.20 |

Brief descriptions of significantly up- and downregulated genes together with descriptions of genes of interest (Table 7)
lit—e14 prophage; like phage T4 late gene expression
ykgA—putative ARAC-type regulatory protein
ykgB—putative membrane protein
ykgL—hypothetical protein
tra5_5—putative IS transposase
tra5_4—transposase insF for insertion sequence IS3
tra5_3—putative transposase for IS3
tra5_2—DLP12 prophage; putative transposase for insertion sequence IS3
tra5_1—putative transposase 5 of IS3
dicB—Qin prophage; inhibitor of cell division
dicF—antisense RNA; inhibits ftsZ
umuD—SOS mutagenesis; error-prone repair; processed to umuD'; forms complex with umuC
emrA—multidrug resistance secretion protein
marB—multiple antibiotic resistance protein
yeiL—stationary phase nitrogen starvation regulator
rspB—putative dehydrogenase, NAD (P)-binding, starvation-sensing protein
ynaF—Rac prophage
djlA—DnaJ-like membrane chaperone protein
yajf—possible NAGC-like transcriptional regulator
ynaF—conserved hypothetical protein, adenine nucleotide binding domain
dtd—D-Tyr-tRNA (Tyr) deacylase
tdcA—transcriptional activator for amino acids degradation (LysR family)
tdcR—threonine dehydratase operon activator protein
cedA—cell division activator
tnaL—tryptophanase leader peptide
ykgM—putative ribosomal protein
cbl—transcriptional regulator cys regulon; accessory regulatory circuit affecting cysM
b0298 putative transposase-related protein
nac—nitrogen assimilation control protein
dnaQ—DNA polymerase III, epsilon subunit (upstream of dnaQ - rnhA: RNase HI, degrades RNA of DNA-RNA hybrids)
yfjN—CP4-57 prophage; putative cell division protein TABLE 7-continued Blast searches for homologous regions (>17 nt) relating to secondary intergenic regions identified in Table 5

| Primary IG region | Secondary Intergenic Region (region of IG involved in similarity) | Tertiary intergenic Region/Gene/ORF | Description | Size (bp) | Homology to Secondary IG number (% similarity) | Expression Level (antilog) | Gene/ORF upstream | Expression Level (antilog) | Gene/ORF downstream | Expression Level (antilog) |
|---|---|---|---|---|---|---|---|---|---|---|
| ykgB—hypothetical protein | | | | | | | | | | |
| prpE—putative acetyl-CoA synthetase of the propionate catabolism operon | | | | | | | | | | |
| codB—cytosine permease/transport (NCS1 family) | | | | | | | | | | |
| seqA—negative modulator of initiation of replication | | | | | | | | | | |
| b2088 transposase insE for insertion sequence IS3 | | | | | | | | | | |
| renD—DLP12 prophage (renD is upstream of emrE (DLP12 prophage; auxiliary multidrug transport protein, methylviologen and ethidium resistance (SMR family)) | | | | | | | | | | |
| b1027 putative transposase-related protein | | | | | | | | | | |
| ykgL—hypothetical protein | | | | | | | | | | |
| eaeH—attaching and effacing protein, pathogenesis factor | | | | | | | | | | |
| yegB—multidrug transport protein (MFS family) | | | | | | | | | | |
| yffP and yffQ—CPZ-55 prophage | | | | | | | | | | |
| ymfG—e14 prophage; putative exisionase | | | | | | | | | | |
| ymfI—e14 prophage | | | | | | | | | | |
| yffQ—CPZ-55 prophage | | | | | | | | | | |
| dbpA—ATP-dependent RNA helicase | | | | | | | | | | |
| yffP—CPZ-55 prophage | | | | | | | | | | |
| yffQ—CPZ-55 prophage | | | | | | | | | | |
| kil—kil protein (killing function) of lamboid prophage Rac | | | | | | | | | | |
| ydaG—Rac Prophage | | | | | | | | | | |

TABLE 8

| Genetic Element | Location | Function | Modified Function |
|---|---|---|---|
| Prophage Systems CP4-6 prophage | | | |
| Ykfl | 262914-263231 262552-262893 (direction = −) | Toxin | Upregulation/structural mimicry will increase persister phenotype. Antagonists will decrease persister phenotype. |
| YafW | 265777-266010 262914-263331 (direction = −) | Anti-toxin | Upregulation will decrease persister phenotype Antagonists will increase persister phenotype |
| E14 prophage | | | |
| Lit | 1197918-1198811 (direction = +) | Phage T4 late gene expression | Upregulation/structural mimicry will increase persister phenotype. Antagonists will decrease persister phenotype. |
| pin | 1208908-1209462 (direction = +) | Inversion element | Upregulation/structural mimicry will increase persister phenotype. Antagonists will decrease persister phenotype. |
| mcrA | 1209569-1210402 (direction = +) | Restriction of DNA at 5 methylcytosine residues | Upregulation/structural mimicry will increase persister phenotype. Antagonists will decrease persister phenotype. |
| intE | 1198902-1200009 (1198902-1200029) (direction = −) | Integrase | Upregulation/structural mimicry will increase persister phenotype. Antagonists will decrease persister phenotype. |
| ymfS | 1207355-1207768 (direction − +) | Unknown | Upregulation/structural mimicry will increase persister phenotype. Antagonists will decrease persister phenotype. |
| Upregulated genes in hotspots | | | |
| ykgA | 315674-316393 (direction = −) | ARAC regulatory protein | Upregulation/structural mimicry will increase persister phenotype. Antagonists will decrease persister phenotype. |
| ykgD | 319451-320305 (direction = +) | ARAC regulatory protein | Upregulation/structural mimicry will increase persister phenotype. Antagonists will decrease persister phenotype. |
| yagI (belongs to the icIR Family) | 4220383-4221246 | IcIR Family = family of transcriptional regulators | Upregulation/structural mimicry will increase persister phenotype. Antagonists will decrease persister phenotype. |
| | yagI = 287628-288386 | yagI = CP4-6 prophage; putative transcriptional regulator (IcIR family) | |
| yagI | 287628-288386 (direction = −) | Putative regulator | Upregulation/structural mimicry will increase persister phenotype. Antagonists will decrease persister phenotype. |
| yagP | 296605-296993 | LysR-type Regulator | Upregulation/structural mimicry will increase persister phenotype. Antagonists will decrease persister phenotype. |
| yahB | 332725-333657 (direction = −) | LysR-type Regulator | Upregulation/structural mimicry will increase persister phenotype. Antagonists will decrease persister phenotype. |
| Large IG's | | | |
| 186 | 291456-302214 (direction = +) | | |
| 199 | 315678-317525 (direction = +) | | |
| 197 | 311564-313580 (direction = +) | | |
| 201 | 317796-319450 (direction = +) | | |
| 205 | 323678-328686 (direction = +) | | |
| 747 | 1198812-1200674 | | |

TABLE 8-continued

| Genetic Element | Location | Function | Modified Function |
|---|---|---|---|
| 870 | 1387920-1390014 (direction = +) | | |
| Classical IG | | | |
| 1602 | 2558087-2558276 (direction = +) | For these classical Intergenic regions we predict that their over-expression will lead to persister status in over-expressing cells and that their nullification will either be lethal or lead to a loss of persister status. | |
| 1484 | 2384852-2384953 (direction = +) | | |
| 2037 | 3267244-3267303 (direction = +) | | |
| 216 | 343158-343399 (direction = +) | | |
| 754 | 1209463-1209568 (direction = +) | | |
| 1604 | 2560014-2560130 (direction = +) | | |
| 1325 | 2057869-2057985 (direction = +) | | |
| 1803 | 2897441-2897509 (direction = +) | | |
| 477 | 745123-745157 (direction = +) | | |
| 873 | 1390915-1391229 (direction = +) | | |

TABLE 9

*E. coli* ORFs and intergenic regions targeted for the generation of overexpression and antisense suppression strains

| Intergenic Region/ORF | Description |
|---|---|
| mcrA | Restriction of DNA at 5-methylcytosine residues. 5-methyl-cytosine-specific restriction endonuclease B. Located with the e14 prophage region. |
| stfE | Putative tail fiber protein. Located with the e14 prophage region. |
| lit | Like phage T4 late gene expression. Located with the e14 prophage region. |
| pin | Inversion of adjacent DNA. Located with the e14 prophage region. |
| IG754 | Intergenic region. Located with the e14 prophage region. |
| yagL | DNA-binding protein. Located with the CP4-6 prophage region. |
| yahL | Hypothetical protein. Located with the CP4-6 prophage region. |
| ykgA | putative araC-type regulatory protein. Located with the CP4-6 prophage region. |
| ykgk | Putative regulator. Located with the CP4-6 prophage region. |
| ykgM | Putative ribosomal protein. Located with the CP4-6 prophage region. |
| IG216 | Intergenic region. Located with the CP4-6 prophage region. |
| IG1325 | Intergenic region |

TABLE 10

Plasmids used in the present study

| Plasmid | Concentration of Selective Agent |
|---|---|
| pUC18 mini-Tn7T-LAC | 100 µg/ml ampicillin, 15 µg/ml gentamycin |
| pUC18R6KTminiTn7T-Lac inducible vector | 100 µg/ml ampicillin, 15 µg/ml gentamycin |
| pGEM T-easy | 100 µg/ml ampicillin |
| pTNS2 | 100 µg/ml ampicillin |

TABLE 11

Primers and thermal cycle conditions used for amplification of target sequences

| Target Sequence | [a]Sense Primer | [b]Antisense Primer | Thermal Cycle Conditions |
|---|---|---|---|
| lit | 5'-agcccaacaatgtagaggttaacg-3' (SEQ ID ID:5) | 5'-ctttaagcgagcggcgga-3' (SEQ ID ID:6) | 96° C. (5 min), followed by 30 cycles of 96° C. (45 s), 55° C. (45 s), 72° C. (60 s) and a final extension of 72° C. (5 min) |
| mcrA | 5'-taaaagtagtattgtcgtg-3' (SEQ ID ID:7) | 5'-tattacgtcttaaatgtgac-3' (SEQ ID ID:8) | 96° C. (5 min), followed by 30 cycles of 96° C. (45 s), 51° C. (45 s), 72° C. (45 s) and a final extension of 72° C. (5 min) |
| pin | 5'-cattcctgcttttaccagg-3' (SEQ ID ID:9) | 5'-caagttgctgttgttttac-3' (SEQ ID ID:10) | 96° C. (5 min), followed by 30 cycles of 96° C. (45 s), 55° C. (45 s), |

TABLE 11-continued

Primers and thermal cycle conditions used for amplification of target sequences

| Targer Sequence | [a]Sense Primer | [b]Antisense Primer | Thermal Cycle Conditions |
|---|---|---|---|
| stfE | 5'-cctggtaaaagcaggaatg-3' (SEQ ID ID:11) | 5'-gcatcaggctgccctcacg-3' (SEQ ID ID:12) | 72° C. (45 s) and a final extension of 72° C. (5 min) 96° C. (5 min), followed by 30 cycles of 96° C. (45 s), 55° C. (45 s), 72° C. (60 s) and a final extension of 72° C. (5 min) |
| yagL | 5'-agaaggacaaacaattatgag-3' (SEQ ID ID:13) | 5'-ctctgcaattagcttctgga-3' (SEQ ID ID:14) | 96° C. (5 min), followed by 30 cycles of 96° C. (45 s), 55° C. (45 s), 72° C. (45 s) and a final extension of 72° C. (5 min) |
| yahL | 5'-cggtgatgtgaaatatcgt-3' (SEQ ID ID:15) | 5'-tgcgattcactctcaggtgga-3' (SEQ ID ID:16) | 96° C. (5 min), followed by 18 cycles of 96° C. (45 s), 60° C. (decreasing 1° C./cycle (45 s), 72° C. (60 s), followed by 15 cycles of 96°C. (45 s), 43° C. (45 s), 72°C. (60 s) and a final extension 72° C. (5 min) |
| ykgA | 5'-tttgccttcgcccttgctat-3' (SEQ ID ID:17) | 5'-ggtgtggcggcctcagtccg-3' (SEQ ID ID:18) | 96° C. (5 min), followed by 30 cycles of 96° C. (45 s), 55° C. (45 s), 72° C. (45 s) and a final extension of 72° C. (5 min) |
| ykgK | 5'-actaaggaaactgaatgcac-3' (SEQ ID ID:19) | 5'-ttgaggacgtgatgtcccag-3' (SEQ ID ID:20) | 96° C. (5 min), followed by 30 cycles of 96° C. (45 s), 56° C. (45 s), 72° C. (45 s) and a final extension of 72° C. (5 min) |
| ykgM | 5'-atgagcatgtatctttatgg-3' (SEQ ID ID:21) | 5'-gcggtacgcagagagttaag-3' (SEQ ID ID:22) | 96° C. (5 min), followed by 30 cycles of 96° C. (45 s), 55° C. (45 s), 72° C. (45 s) and a final extension of 72° C. (5 min) |
| IG216 | 5'-atgctgcgcggtgatgtgaa-3' (SEQ ID ID:23) | 5'-tgctttgttgcgtatatggc-3' (SEQ ID ID:24) | 96° C. (5 min), followed by 18 cycles of 96° C. (45 s), 60° C. (decreasing 1° C./cycle (45 s), 72° C. (60 s), followed by 15 cycles of 96°C. (45 s), 43° C. (45 s), 72°C. (60 s) and a final extension 72° C. (5 min) |
| IG754 | 5'-tgcagggatatataaag-3' (SEQ ID ID:25) | 5'-tcagctttcagttcaattcc-3' (SEQ ID ID:26) | 96° C. (5 min), followed by 14 cycles of 96° C. (30 s), 53° C. (decreasing 1° C./cycle (30 s), 72° C. (30 s), followed by 16 cycles of 96°C. (30 s), 45° C. (30 s), 72°C. (30 s) and a final extension 72° C. (5 min) |
| IG1325 | 5'-tcgccgttaagatgtgcctc-3' (SEQ ID ID:27) | 5'-gcagtgaagaggaaattgat-3' (SEQ ID ID:28) | 96° C. (5 min), followed by 16 cycles of 96° C. (45 s), 65° C. (decreasing 1° C./cycle (45 s), 72° C. (45 s), followed by 16 cycles of 96°C. (45 s), 49° C. (45 s), 72°C. (45 s) and a final extension 72° C. (5 min) |

[a]BamH1 (ggatcc) or Xho1 (ctcgag) restriction sites added to 5'end for the generation of overexpression or deletion sense primers respectively.
[b]Xho1 (ctcgag) or BamH1 (ggatcc) restriction sites added to 5'end for the generation of overexpression or deletion antisense primers respectively.

TABLE 12

Progress achieved in the generation of overexpression *E. coli* strains

| Target sequence | Primary PCR | pGEM T-easy cloning | Sequence verification | Cloning into pUC18R6KTminiTn7T-Lac inducible vector | Mobilisation into target CC118 recipient strain | Verification of Generated strains | Comments |
|---|---|---|---|---|---|---|---|
| e14 region | | | | | | | |
| mcrA | ✓ | ✓ | ✓ | ✓ | ✓ | ✓ | |
| stfE | ✓ | ✓ | ✓ | X | | | Prone to recombination |
| IG754 | ✓ | X | | | | | |
| lit | ✓ | ✓ | ✓ | ✓ | ✓ | ✓ | |
| pin | ✓ | ✓ | ✓ | ✓ | ✓ | ✓ | |
| CP4-6 region | | | | | | | |
| ykgK | ✓ | ✓ | ✓ | ✓ | ✓ | ✓ | |

TABLE 12-continued

Progress achieved in the generation of overexpression E. coli strains

| Target sequence | Primary PCR | pGEM T-easy cloning | Sequence verification | Cloning into pUC18R6KTminiTn7T-Lac inducible vector | Mobilisation into target CC118 recipient strain | Verification of Generated strains | Comments |
|---|---|---|---|---|---|---|---|
| yahL | X | | | | | | |
| ykgM | ✓ | ✓ | ✓ | ✓ | ✓ | ✓ | |
| IG216 | X | | | | | | |
| yagL | ✓ | ✓ | ✓ | ✓ | ✓ | ✓ | |
| ykgA | ✓ | ✓ | ✓ | X | | | Prone to recombination |
| Additional | | | | | | | |
| IG1325 | ✓ | X | | | | | |

TABLE 13

Progress achieved in the generation of suppression E. coli strains

| Target Sequence | Primary PCR | pGEM T-easy cloning | Sequence verification | Cloning into pUC18R6KTminiTn7T-Lac inducible vector | Mobilisation into target CC118 recipient strain | Verification of Generated strains | Comments |
|---|---|---|---|---|---|---|---|
| e14 region | | | | | | | |
| mcrA | ✓ | ✓ | ✓ | ✓ | ✓ | X | No candidates with correct phenotype |
| stfE | ✓ | ✓ | ✓ | X | | | Prone to recombination |
| IG754 | ✓ | X | | | | | |
| lit | ✓ | ✓ | ✓ | ✓ | ✓ | ✓ | |
| pin | ✓ | ✓ | ✓ | ✓ | ✓ | ✓ | |
| CP4-6 region | | | | | | | |
| ykgK | ✓ | ✓ | ✓ | ✓ | ✓ | ✓ | |
| yahL | Not attempted | | | | | | |
| ykgM | ✓ | ✓ | ✓ | ✓ | ✓ | ✓ | |
| IG216 | Not attempted | | | | | | |
| yagL | ✓ | ✓ | ✓ | ✓ | ✓ | X | No candidates with correct phenotype |
| ykgA | ✓ | ✓ | ✓ | X | | | Prone to recombination |
| Additional | | | | | | | |
| IG1325 | ✓ | X | | | | | |

TABLE 14

Target genes for which conditional overexpression (+) or antisense suppression (−) E. coil strains were generated and validated
Target Sequence lit (+)
lit (−)
mcrA (+)
pin (+)
pin (−)
yagL (+)
ykgK (+)
ykgK (−)
ykgM (+)
ykgM (−)

TABLE 15

Fold change in survival of exponential phase E. coil CC118 overexpression and suppression mutants relative to the parental E. coli CC118 strain following exposure to 9 μg/ml cetrimide for 1 h. IPTG (0.1 mM) added to early exponential phase cultures for 1.75 h prior to harvesting cultures.

| Strain | Fold Change in persister fraction | Standard Deviation |
|---|---|---|
| mcrA (+) | 2.82 fold increase | 0.001709 |
| lit (+) | 3.05 fold increase | 0.015386 |
| lit (−) | 1.31 fold increase | 0.006354 |
| pin (+) | 10.38 fold increase | 0.00244 |
| pin (−) | 18.98 fold increase | 0.007089 |
| yagL (+) | 1.01 fold decrease | 7.14E−05 |
| ykgK (+) | 22.85 fold increase | 0.008 |
| ykgK (−) | 5.35 fold decrease | 9.09E−05 |
| ykgM (+) | 1.65 fold decrease | 0.022368 |
| ykgM (−) | 1.83 fold decrease | 0.00719 |

TABLE 16

Fold change, relative to the parental *E. coil* CC118 strain, in persister fraction of stationary phase *E. coil* CC118 antisense suppression mutants following exposure to 9 µg/ml cetrimide for 1 h. IPTG (0.1 mM) added to early exponential phase cultures for 14.5 h prior to harvesting cultures.

| Strain | Fold Change in persister fraction | Standard Deviation |
|---|---|---|
| lit (−) | 4.08 fold decrease | 8.67E−05 |
| pin (−) | No persisters detected | 0 |
| ykgK (−) | No persisters detected | 0 |
| ykgM (−) | No persisters detected | 0 |

TABLE 17

Sequence Homology between *E. coli* persister genes mcrA, lit, pin, ykgK and ykgM with additional bacteria (BLAST searches conducted on Jun. 8, 2006 using the NCBI database).

| *E. coli* persister gene | Length (nt) of persister gene | Region of persister gene involved in sequence homology | Bacteria with sequence homology to *E. coli* persister gene | Length (nt) of homology to persister gene (% homology) | Position of homology within homologous sequence (gene and description detailed where reported on NCBI database) |
|---|---|---|---|---|---|
| mcrA | 834 | 229-250$^{th}$ nt | *Colobus guereza* clone CH272-163G5, complete sequence | 22/22 (100%) | 5610-5589$^{th}$ nt |
| | | 541-562$^{th}$ nt | *Strongylocentrotus purpurarus* similar to vesicle transport through interaction with t-SNAREs homolog IB (LOC587367), partial mRNA | 22/22 (100%) | 112-133$^{th}$ nt |
| | | 727-755$^{th}$ nt | *Pseudomonas fluorescens* PfO-1, complete genome | 27/29 (93%) | 5229283-5229311$^{th}$ nt (pfl 4628: HNH endonuclease) |
| | | 204-224$^{th}$ nt | *Chlamydia trachomatis* A/HAR-13, complete genome | 21/21 (100%) | 310761-310741$^{th}$ nt (CTA0299: hypothetical membrane associated protein) |
| | | 425-445$^{th}$ nt | Uncultured bacterium 106 clone EBAC750-01B07 genomic sequence | 21/21 (100%) | 39536-39556$^{th}$ nt |
| lit | 894 | No homologous sequences detected within the DNA of other bacteria | | | |
| pin | 555 | 1-539$^{th}$ nt | *Shigella dysenteriae* Sd197, complete genome | 506/539 (93%) | 2554819-2554281$^{th}$ nt (SDY 2752: DNA-invertase) |
| | | 2-56$^{th}$ nt | *Shigella dysenteriae* Sd197, complete genome | 51/59 (86%) | 1746071-1746017$^{th}$ nt (SDY 1916: putative DNA-invertase) |
| | | 162-203$^{th}$ nt | *Shigella dysenenae* Sd197, complete genome | 38/42 (90%) | 1745911-1745870$^{th}$ nt (SDY 1916: putative DNA-invertase) |
| | | 1-553$^{th}$ nt | *Eschenchia coli* O157: H7 str. Sakai DNA, complete genome | 514/553 (92%) | 306891-307443$^{th}$ nt (ECs 0284: DNA-invertase) |
| | | 1-98$^{th}$ nt | *Eschenchia coli* O157: H7 str. Sakai DNA, complete genome | 88/98 (89%) | 5074651-5074748 (ECs4992: putative DNA-invertase) |
| | | 130-264$^{th}$ nt | *Escherichia coli* O157: H7 str. Sakai DNA, complete genome | 114/135 (84%) | 3505470-3505336$^{th}$ nt (ECs3516: hypothetical protein) |
| | | 322-365$^{th}$ nt | *Escherichia coli*, O157: H7 str. Sakai DNA, complete genome | 39/44 (88%) | 5074972-5075015$^{th}$ nt (ECs4992: putative DNA-invertase) |
| | | 1-539$^{th}$ nt | *Shigella flexneri* 5 str. 8401, complete genome | 503/539 (93%) | 2681077-2680539$^{th}$ nt (pin: inversion of adjacent DNA; at locus of e14 element) |
| | | 1-63$^{th}$ nt | *Shigella flexneri* 5 str. 8401, complete genome | 61/63 (96%) | 777174-777236$^{th}$ nt (Features flanking this part of subject sequence: |

TABLE 17-continued

Sequence Homology between *E. coli* persister genes mcrA, lit, pin, ykgK and ykgM with additional bacteria (BLAST searches conducted on Jun. 8, 2006 using the NCBI database).

| E. coli persister gene | Length (nt) of persister gene | Region of persister gene involved in sequence homology | Bacteria with sequence homology to E. coli persister gene | Length (nt) of homology to persister gene (% homology) | Position of homology within homologous sequence (gene and description detailed where reported on NCBI database) |
|---|---|---|---|---|---|
| | | 1-512$^{th}$ nt | *Shigella sonnei* Ss046, complete genome | 482/512 (94%) | 2804477-2803966$^{th}$ nt (Features flanking this part of subject sequence: 385 bp at 5' side: conserved hypothetical protein 491 bp at 3' side: invasion plasmid antigen) |
| | | 1-63$^{th}$ nt | *Shigella sonnei* Ss046, complete genome | 61/63 (96%) | 782988-783050$^{th}$ nt (Features flanking this part of subject sequence: 32 bp at 5' side: IS1 ORF 329 bp at 3' side: putative isomerase) |
| | | 130-264$^{th}$ nt | *Shigella sonnei* Ss046, complete genome | 113/135 (83%) | 2942313-2942179$^{th}$ nt (SSO 2797: conserved hypothetical protein) |
| | | 162-232$^{th}$ nt | *Shigella sonnei* Ss046, complete genome | 61/71 (85%) | 1986745-1986675$^{th}$ nt (Features flanking this part of subject sequence: 150 bp at 5' side: unknown protein encoded within prophage 389 bp at 3' side: putative bacteriophage tail protein) |
| | | 2-56$^{th}$ nt | *Shigella sonnei* Ss046, complete genome | 49/55 (89%) | 1986905-1986851$^{th}$ nt (flanking this part of subject sequence: 326 bp at 5' side: unknown protein encoded within prophage 229 bp at 3' side: putative bacteriophage tail protein) |
| | | 351-539$^{th}$ nt | *Salmonella enterica* serovar Typhi (*Salmonella typhi*) strain CT18, complete chromosome; segment 8/20 | 174/189 (92%) | 82875-82687$^{th}$ nt (STY2012: DNA-invertase (pseudogene)) |
| | | 1-221$^{th}$ nt | *Salmonella enterica* serovar Typhi (*Salmonella typhi*) strain CT18, complete chromosome; segment 15/20 | 194/221 (87%) | 77120-77340$^{th}$ nt (STY3658: possible competence-related protein, (pseudogene) DNA-invertase) |
| | | 280-365$^{th}$ nt | *Salmonella enterica* serovar Typhi (*Salmonella typhi*) strain CT18, complete chromosome; segment 15/20 | 77/86 (89%) | 77399-77484$^{th}$ nt ((STY3660: possible competence-related protein (pseudogene) DNA-invertase) |
| | | 1-221$^{th}$ nt | *Shigella boydii* Sb227, complete genome | 193/221 (87%) | 782871-783091$^{th}$ nt (pin: inversion of adjacent DNA; at locus of e14 element |
| | | 1-95$^{th}$ nt | *Shigella boydii* Sb227, complete genome | 89/95 (93%) | 666329-666423$^{th}$ nt (Features flanking this part of subject sequence: 491 bp at 5' side: invasion plasmid a ntigen 296 bp at 3' side: putative isomerase) |
| | | 295-365$^{th}$ nt | *Shigella boydii* Sb227, complete genome | 64/71 (90%) | 1371156-1371086$^{th}$ nt (SBO 1391: putative DNA-invertase) |
| | | 280-365$^{th}$ nt | *Shigella boydii* Sb227, complete genome | 74/86 (86%) | 783150-783235$^{th}$ nt (pin: inversion of adjacent DNA; at locus of e14 element) |
| | | 2-47$^{th}$ nt | *Shigella boydii* Sb227, complete genome | 42/46 (91%) | 1371449-1371404$^{th}$ nt (SBO 1391: putative DNA-invertase) |

TABLE 17-continued

Sequence Homology between *E. coli* persister genes mcrA, lit, pin,
ykgK and ykgM with additional bacteria (BLAST searches conducted on Jun. 8, 2006
using the NCBI database).

| *E. coli* persister gene | Length (nt) of persister gene | Region of persister gene involved in sequence homology | Bacteria with sequence homology to *E. coli* persister gene | Length (nt) of homology to persister gene (% homology) | Position of homology within homologous sequence (gene and description detailed where reported on NCBI database) |
|---|---|---|---|---|---|
| | | 7-276$^{th}$ nt | *Salmonella typhimunum* LT2, section 127 of 220 of the complete genome | 225/270 (83%) | 7922-7653$^{th}$ nt |
| | | 307-365$^{th}$ nt | *Pectobacterium carotovorum* genes for tail sheath protein, tail core protein, baseplate, tail fiber and recombinase, complete cds | 54/59 (91%) | 17419-17477$^{th}$ nt |
| | | 295-368$^{th}$ nt | *Salmonella enterica* subsp. enterica serovar Paratyphi A str. ATCC 9150 | 63/74 (85%) | 1260059-1260132$^{th}$ nt (Features flanking this part of subject sequence: 540 bp at 5' side: hypothetical periplasmic protein 182 bp at 3' side: hypothetical protein) |
| | | 280-344$^{th}$ nt | *Photorhabdus luminescens* subsp. laumondii TTO1 complete genome; segment 1/17 | 54/65 (83%) | 26170-26106$^{th}$ nt (hin: DNA-invertase HIN) |
| | | 337-365$^{th}$ nt | *Xylella fastidiosa* 9a5c, complete genome | 27/29 (93%) | 1935163-1935135$^{th}$ nt (XF2028: DNA invertase) |
| | | 172-203$^{th}$ nt | *Nitrosomonas europaea* ATCC 19718, complete genome segment 6/10 | 29/32 (90%) | 113239-113208$^{th}$ nt (NE1521: site-specific recombinase) |
| ykgk | 591 | 1-591$^{th}$ nt | *Shigella boydii* Sb227, complete genome | 585/591 (98%) | 237999-238589$^{th}$ nt (ykgK: putative regulator) |
| | | 1-591$^{th}$ nt | *Eschenchia coli* O157: H7 str. Sakai DNA, complete genome | 573/591 (96%) | 343744-343154$^{th}$ nt (ECs0324: putative regulator) |
| | | 210-229$^{th}$ nt | *Clostridium tetani* E88, complete genome | 20/20 (100%) | 67411-67430$^{th}$ nt (CTC00110: conserved protein) |
| ykgM | 264 | 1-264$^{th}$ nt | *Shigella boydii* Sb227, complete genome | 263/264 (99%) | 236559-236822$^{th}$ nt (ykgM: putative ribosomal protein) |
| | | 1-264$^{th}$ nt | *Escherichia coli* O157: H7 str. Sakai DNA, complete genome | 261/264 (98%) | 345185-344922$^{th}$ nt putative (ECs0327: ribosomal protein) |
| | | 10-243$^{th}$ nt | *Escherichia coli* O157: H7 str. Sakai DNA, complete genome | 195/234 (83%) | 1396603-1396836$^{th}$ nt (ECs1330: ribosomal protein L31-like protein) |
| | | 1-55$^{th}$ nt | *Yersinia pestis* biovar Medievalis str. 91001 section 3 of 16 of the complete genome | 48/55 (87%) | 279318-279264$^{th}$ nt (rpmE2: putative ribosomal protein) |
| | | 1-55$^{th}$ nt | *Yersinia pestis* Antiqua, complete genome | 48/55 (87%) | 2927168-2927222$^{th}$ nt (YPA_2629: putative ribosomal protein) |
| | | 1-55$^{th}$ nt | *Yersinia pseudotuberculosis* IP32953 genome, complete sequence | 48/55 (87%) | 1178666-1178612$^{th}$ nt (ykgM: putative ribosomal protein L31-like protein) |
| | | 13-69$^{th}$ nt | *Vibrio parahaemolyticus* RIMD 2210633 DNA, chromosome 1, complete sequence | 49/57 (85%) | 2442718-2442662$^{th}$ nt (VP2331: ribosomal protein, L31P family) |
| | | 13-56$^{th}$ nt | *Vibrio vulnificus* CMCP6 chromosome I complete sequence | 39/44 (88%) | 1837201-1837244$^{th}$ nt (VV11840: Ribosomal protein L31 family) |
| | | 82-161$^{th}$ nt | *Salmonella enterica* serovar Typhi (*Salmonella typhi*) strain CT18, complete chromosome; segment 3/20 | 65/80 (81%) | 294-373$^{th}$ nt (ykgM: putative 50 s ribosomal protein L31 (second copy)) |

TABLE 17-continued

Sequence Homology between *E. coli* persister genes mcrA, lit, pin, ykgK and ykgM with additional bacteria (BLAST searches conducted on Jun. 8, 2006 using the NCBI database).

| *E. coli* persister gene | Length (nt) of persister gene | Region of persister gene involved in sequence homology | Bacteria with sequence homology to *E. coli* persister gene | Length (nt) of homology to persister gene (% homology) | Position of homology within homologous sequence (gene and description detailed where reported on NCBI database) |
|---|---|---|---|---|---|
| | | 82–161$^{th}$ nt | *Salmonella enterica* subsp. enterica serovar Typhi Ty2, complete genome | 65/80 (81%) | 2461807-2461728$^{th}$ nt. (rpmE: putative 50 s ribosomal protein L31) |
| | | 146–173$^{th}$ nt | *Listeria monocytogenes* strain EGD, complete genome segment 11/12 | 26/28 (92%) | 229730-229703$^{th}$ nt (rpmE: ribosomal protein L31) |

We claim:

1. A method of identifying compounds that alter bacterial persister status, the method comprising the step of identifying compounds that modulate the expression of a gene selected from *E. coli* genes mcrA, lit, pin, ykgM and ykgK or inhibit or enhance the functional activity of the protein products of these genes.

2. The method of claim 1 wherein the compound suppresses ykgK gene expression or the functional activity of the ykgK gene products.

3. The method of claim 1 where in the compound suppresses ykgK gene expression or the functional activity of the ykgK gene expression products.

4. The method of claim 1 wherein the compound enhances ykgK gene expression or the functional activity of the ykgK gene expression products.

5. The method of claim 1 wherein the compound suppresses or enhances ykgM gene expression or the functional activity of the ykgM gene expression products.

6. The method of claim 1 wherein the compound enhances mcrA gene expression or the functional activity of the mcrA gene expression products.

7. The method of claim 1 wherein the compound enhances or suppresses lit gene expression or the functional activity of the lit gene expression products.

8. The method of claim 1 wherein the compound enhances or suppresses the pin gone expression or the functional activity of the pin gene expression products.

* * * * *

UNITED STATES PATENT AND TRADEMARK OFFICE
CERTIFICATE OF CORRECTION

| | |
|---|---|
| PATENT NO. | : 7,572,903 B1 |
| APPLICATION NO. | : 11/505644 |
| DATED | : August 11, 2009 |
| INVENTOR(S) | : Peter Gilbert et al. |

It is certified that error appears in the above-identified patent and that said Letters Patent is hereby corrected as shown below:

Column 72, Line 56: replace "gone" with --gene--

Signed and Sealed this

Twenty-second Day of September, 2009

David J. Kappos
*Director of the United States Patent and Trademark Office*

SEQUENCE LISTING

<160> NUMBER OF SEQ ID NOS: 28

<210> SEQ ID NO 1
<211> LENGTH: 19
<212> TYPE: DNA
<213> ORGANISM: Artificial
<220> FEATURE:
<223> OTHER INFORMATION: SYNTHETIC OLIGONUCLEOTIDE

<400> SEQUENCE: 1
gtgtggaatt gtgagcgga                                                    19

<210> SEQ ID NO 2
<211> LENGTH: 19
<212> TYPE: DNA
<213> ORGANISM: Artificial
<220> FEATURE:
<223> OTHER INFORMATION: SYNTHETIC OLIGONUCLEOTIDE

<400> SEQUENCE: 2
gaactgggtg tagcgtcgt                                                    19

<210> SEQ ID NO 3
<211> LENGTH: 23
<212> TYPE: DNA
<213> ORGANISM: Artificial
<220> FEATURE:
<223> OTHER INFORMATION: SYNTHETIC OLIGONUCLEOTIDE

<400> SEQUENCE: 3
cagcataact ggactgattt cag                                               23

<210> SEQ ID NO 4
<211> LENGTH: 20
<212> TYPE: DNA
<213> ORGANISM: Artificial
<220> FEATURE:
<223> OTHER INFORMATION: SYNTHETIC OLIGONUCLEOTIDE

<400> SEQUENCE: 4
cacgctgaag cctacgctgc                                                   20

<210> SEQ ID NO 5

```
<211> LENGTH: 24
<212> TYPE: DNA
<213> ORGANISM: Artificial
<220> FEATURE:
<223> OTHER INFORMATION: PCR PRIMER

<400> SEQUENCE: 5
agcccaacaa tgtagaggtt aacg                                            24

<210> SEQ ID NO 6
<211> LENGTH: 18
<212> TYPE: DNA
<213> ORGANISM: Artificial
<220> FEATURE:
<223> OTHER INFORMATION: PCR PRIMER

<400> SEQUENCE: 6
ctttaagcga gcggcgga                                                   18

<210> SEQ ID NO 7
<211> LENGTH: 19
<212> TYPE: DNA
<213> ORGANISM: Artificial
<220> FEATURE:
<223> OTHER INFORMATION: PCR PRIMER

<400> SEQUENCE: 7
taaaagtagt attgtcgtg                                                  19

<210> SEQ ID NO 8
<211> LENGTH: 20
<212> TYPE: DNA
<213> ORGANISM: Artificial
<220> FEATURE:
<223> OTHER INFORMATION: PCR PRIMER

<400> SEQUENCE: 8
tattacgtct taaatgtgac                                                 20

<210> SEQ ID NO 9
<211> LENGTH: 19
<212> TYPE: DNA
<213> ORGANISM: Artificial
<220> FEATURE:
<223> OTHER INFORMATION: PCR PRIMER

<400> SEQUENCE: 9
cattcctgct tttaccagg                                                  19

<210> SEQ ID NO 10
<211> LENGTH: 19
<212> TYPE: DNA
<213> ORGANISM: Artificial
<220> FEATURE:
<223> OTHER INFORMATION: PCR PRIMER

<400> SEQUENCE: 10
caagttgctg ttgttttac                                                  19

<210> SEQ ID NO 11
<211> LENGTH: 19
<212> TYPE: DNA
<213> ORGANISM: Artificial
<220> FEATURE:
<223> OTHER INFORMATION: PCR PRIMER

<400> SEQUENCE: 11
```
cctggtaaaa gcaggaatg                                        19

<210> SEQ ID NO 12
<211> LENGTH: 19
<212> TYPE: DNA
<213> ORGANISM: Artificial
<220> FEATURE:
<223> OTHER INFORMATION: PCR PRIMER

<400> SEQUENCE: 12
gcatcaggct gccctcacg                                        19

<210> SEQ ID NO 13
<211> LENGTH: 21
<212> TYPE: DNA
<213> ORGANISM: Artificial
<220> FEATURE:
<223> OTHER INFORMATION: PCR PRIMER

<400> SEQUENCE: 13
agaaggacaa acaattatga g                                     21

<210> SEQ ID NO 14
<211> LENGTH: 20
<212> TYPE: DNA
<213> ORGANISM: Artificial
<220> FEATURE:
<223> OTHER INFORMATION: PCR PRIMER

<400> SEQUENCE: 14
ctctgcaatt agcttctgga                                       20

<210> SEQ ID NO 15
<211> LENGTH: 19
<212> TYPE: DNA
<213> ORGANISM: Artificial
<220> FEATURE:
<223> OTHER INFORMATION: PCR PRIMER

<400> SEQUENCE: 15
cggtgatgtg aaatatcgt                                        19

<210> SEQ ID NO 16
<211> LENGTH: 21
<212> TYPE: DNA
<213> ORGANISM: Artificial
<220> FEATURE:
<223> OTHER INFORMATION: PCR PRIMER

<400> SEQUENCE: 16
tgcgattcac tctcaggtgg a                                     21

<210> SEQ ID NO 17
<211> LENGTH: 19
<212> TYPE: DNA
<213> ORGANISM: Artificial
<220> FEATURE:
<223> OTHER INFORMATION: PCR PRIMER

<400> SEQUENCE: 17
tttgccttcg ccttgctat                                        19

<210> SEQ ID NO 18
<211> LENGTH: 20
<212> TYPE: DNA

-continued

<213> ORGANISM: Artificial
<220> FEATURE:
<223> OTHER INFORMATION: PCR PRIMER

<400> SEQUENCE: 18
ggtgtggcgg cctcagtccg                                               20

<210> SEQ ID NO 19
<211> LENGTH: 20
<212> TYPE: DNA
<213> ORGANISM: Artificial
<220> FEATURE:
<223> OTHER INFORMATION: PCR PRIMER

<400> SEQUENCE: 19
actaaggaaa ctgaatgcac                                               20

<210> SEQ ID NO 20
<211> LENGTH: 20
<212> TYPE: DNA
<213> ORGANISM: Artificial
<220> FEATURE:
<223> OTHER INFORMATION: PCR PRIMER

<400> SEQUENCE: 20
ttgaggacgt gatgtcccag                                               20

<210> SEQ ID NO 21
<211> LENGTH: 20
<212> TYPE: DNA
<213> ORGANISM: Artificial
<220> FEATURE:
<223> OTHER INFORMATION: PCR PRIMER

<400> SEQUENCE: 21
atgagcatgt atctttatgg                                               20

<210> SEQ ID NO 22
<211> LENGTH: 20
<212> TYPE: DNA
<213> ORGANISM: Artificial
<220> FEATURE:
<223> OTHER INFORMATION: PCR PRIMER

<400> SEQUENCE: 22
gcggtacgca gagagttaag                                               20

<210> SEQ ID NO 23
<211> LENGTH: 20
<212> TYPE: DNA
<213> ORGANISM: Artificial
<220> FEATURE:
<223> OTHER INFORMATION: PCR PRIMER

<400> SEQUENCE: 23
atgctgcgcg gtgatgtgaa                                               20

<210> SEQ ID NO 24
<211> LENGTH: 20
<212> TYPE: DNA
<213> ORGANISM: Artificial
<220> FEATURE:
<223> OTHER INFORMATION: PCR PRIMER

<400> SEQUENCE: 24
tgctttgttg cgtatatggc                                               20

<210> SEQ ID NO 25
<211> LENGTH: 18
<212> TYPE: DNA
<213> ORGANISM: Artificial
<220> FEATURE:
<223> OTHER INFORMATION: PCR PRIMER

<400> SEQUENCE: 25
tgcaggggat aaataaag                                                 18

<210> SEQ ID NO 26
<211> LENGTH: 20
<212> TYPE: DNA
<213> ORGANISM: Artificial
<220> FEATURE:
<223> OTHER INFORMATION: PCR PRIMERS

<400> SEQUENCE: 26
tcagctttca gttcaattcc                                               20

<210> SEQ ID NO 27
<211> LENGTH: 20
<212> TYPE: DNA
<213> ORGANISM: Artificial
<220> FEATURE:
<223> OTHER INFORMATION: PCR PRIMERS

<400> SEQUENCE: 27
tcgccgttaa gatgtgcctc                                               20

<210> SEQ ID NO 28
<211> LENGTH: 20
<212> TYPE: DNA
<213> ORGANISM: Artificial
<220> FEATURE:
<223> OTHER INFORMATION: PCR PRIMERS

<400> SEQUENCE: 28
gcagtgaaga ggaaattgat                                               20